(12) United States Patent
Aferzon

(10) Patent No.: US 8,747,443 B2
(45) Date of Patent: Jun. 10, 2014

(54) SPINAL PLATE WITH COMPRESSION LOCKING

(75) Inventor: Joseph Aferzon, Avon, CT (US)

(73) Assignee: International Spinal Innovations, LLC, West Hartford, CT (US)

( * ) Notice: Subject to any disclaimer, the term of this patent is extended or adjusted under 35 U.S.C. 154(b) by 506 days.

(21) Appl. No.: 12/908,814

(22) Filed: Oct. 20, 2010

(65) Prior Publication Data

US 2011/0093016 A1    Apr. 21, 2011

Related U.S. Application Data

(60) Provisional application No. 61/279,351, filed on Oct. 21, 2009, provisional application No. 61/280,950, filed on Nov. 12, 2009.

(51) Int. Cl.
*A61B 17/80* (2006.01)

(52) U.S. Cl.
USPC .......................................... 606/295; 606/289

(58) Field of Classification Search
CPC .................................................. A61B 17/8042
USPC ............... 606/280–299, 71; 623/17.11–17.16
See application file for complete search history.

(56) References Cited

U.S. PATENT DOCUMENTS

| | | | |
|---|---|---|---|
| 5,578,034 A | 11/1996 | Estes | |
| 6,695,846 B2 | 2/2004 | Richelsoph et al. | |
| 7,063,701 B2 | 6/2006 | Michelson | |
| 7,288,094 B2 | 10/2007 | Lindemann et al. | |
| 7,306,605 B2 | 12/2007 | Ross | |
| 7,547,306 B2 | 6/2009 | Michelson | |
| 2002/0022843 A1* | 2/2002 | Michelson | 606/70 |
| 2003/0093082 A1* | 5/2003 | Campbell et al. | 606/104 |
| 2003/0187440 A1 | 10/2003 | Richelsoph et al. | |
| 2006/0195104 A1 | 8/2006 | Schlafli et al. | |
| 2006/0293669 A1* | 12/2006 | Lindemann et al. | 606/69 |
| 2007/0055253 A1 | 3/2007 | Orbay et al. | |
| 2009/0062863 A1 | 3/2009 | Peppers | |
| 2009/0149888 A1 | 6/2009 | Abdelgany | |
| 2009/0192549 A1 | 7/2009 | Sanders et al. | |

OTHER PUBLICATIONS

International Search Report and Written Opinion issued for PCT/US2010/053448 issued on Dec. 21, 2010.

\* cited by examiner

*Primary Examiner* — Nicholas Woodall
(74) *Attorney, Agent, or Firm* — Hoffmann & Baron, LLP

(57) ABSTRACT

A spinal plate system includes a screw, spinal plate and cap. A head of the screw includes a portion of a first sphere that has a first center and a portion of a second sphere that has a second center approximately concentric with the first center. A body of the screw extends from the first sphere. The spinal plate includes an opening through the spinal plate and an associated recess in the spinal plate that is eccentric with the opening. The cap includes an alignment opening and is configured to be rotationally engaged in the recess between a first rotational configuration and a second rotational configuration. In the first rotational configuration, the body threads into a vertebra in a selected trajectory through the alignment opening and the opening in the spinal plate and the head engages at least a portion of the opening in the selected trajectory. In the second rotational configuration, the cap compresses the second sphere into the first sphere approximately through its center such that the head is compressed into the engaged portion of the opening.

17 Claims, 12 Drawing Sheets

SPINAL PLATE WITH COMPRESSION LOCKING

CROSS-REFERENCE TO RELATED APPLICATIONS

This application claims priority to and benefit of U.S. Provisional Patent Application Ser. No. 61/279,351, filed on Oct. 21, 2009, and U.S. Provisional Patent Application Ser. No. 61/280,950, filed on Nov. 12, 2009, which are incorporated herein by reference in their entireties.

BACKGROUND

1. Field of Technology

This application relates generally to spinal fixation. More specifically, this application is directed to a spinal plate with compression locking and a method of fixating vertebrae using the spinal plate with compression locking.

2. Brief Description of Related Art

Spinal surgery frequently requires fixation of the spinal column, e.g., spinal fixation of a plurality of spinal vertebrae. Spinal vertebrae are bony cylindrical structures that are located in front of the spinal cord and nerves; they contribute to the structural support of the axial skeleton. Anterior or lateral spinal fixation can be used to fixate vertebrae along the cervical, thoracic and lumbar regions of the spinal column.

Generally, a spinal plate and a plurality of screws are used for spinal fixation. The spinal plate is placed over multiple vertebrae to be fixated with respect to one another. Generally, the openings through the spinal plate have matching geometry to the screws, allowing screw angulations over a range of trajectories through the spinal plate. The screws anchor the spinal plate to the vertebrae. The screw angulations provide for various screw placements given different anatomy of patients and locations along the spinal column.

Screw back-out that results from the loosing of the screws with respect to the spinal plate is a significant concern. When screws loosen, their screw heads pivot about the openings of the spinal plate with spinal plate motion in respect to the vertebrae. Unrestricted movement can result in screw dislodgement with respect to the spinal plate, jeopardizing the patient's health.

Multiple back-out mechanisms have been proposed. However, the back-out mechanisms do not adequately lock (rigidly fixate) the screws (via their screw heads) in their trajectories with respect to the spinal plate, but rather attempt to prevent dislodgement of the screws from the spinal plate. For rigid fixation versus back-out prevention, the potential for pivoting of screw heads about the openings in the spinal plate should be restrained.

Furthermore, the foregoing back-out mechanisms usually include multiple components that require complex engagement with respect to the spinal plate and screws, blocking visualization of the underlying vertebra and increasing undesirably the size of the spinal plate.

SUMMARY

In accordance with an embodiment, a spinal plate system is provided. The spinal plate system includes a screw, spinal plate and cap.

The screw includes a head and a threaded body. The head includes a portion of a first sphere that has a first center and a portion of a second sphere that has a second center approximately concentric with the first center. The body of the screw extends from the first sphere.

The spinal plate includes an opening through the spinal plate and an associated recess in the spinal plate that is eccentric with the opening.

The cap includes an alignment opening and is configured to be rotationally engaged in the recess between a first rotational configuration and a second rotational configuration.

The first rotational configuration enables the threaded body of the screw to be threaded into a vertebra in a selected trajectory through the alignment opening and the opening in the spinal plate and the head of the screw to engage at least a portion of the opening in the selected trajectory.

The second rotational configuration enables the cap to compress the second sphere into the first sphere approximately through its center such that the head of the screw is compressed into the engaged portion of the opening.

In accordance with another embodiment, a spinal screw is provided. The spinal screw includes a head and a threaded body.

The head of the screw is defined by a portion of a first sphere that has a first center and a portion of a second sphere that has a second center approximately concentric with the first center. The threaded body extends from the first sphere.

The head of the screw is configured such that the portion of the first sphere can be compressed into a receiving opening approximately through its center via compression of the second sphere.

In accordance with a further embodiment, a method of fixating vertebrae in a spinal column is provided.

In accordance with the method, a spinal plate engaging a cap in a first rotational configuration is inserted over a vertebra. The spinal plate includes an opening through the spinal plate and an associated recess in the spinal plate that is eccentric with the opening. The cap is rotationally engaged in the recess and includes an alignment opening that is aligned with the opening in the spinal plate.

A screw is threaded into the vertebra in a selected trajectory through the alignment opening and the opening in the spinal plate. The screw including a spherically-shaped head that engages at least a portion of the opening in the selected trajectory.

The cap is rotated in the recess to compress the spherically-shaped head of the screw approximately through its center into the engaged portion of the opening.

For a more thorough understanding of the present invention, reference is made to the following description, taken in conjunction with the accompanying drawings, and its scope will be pointed out in the appended claims.

BRIEF DESCRIPTION OF THE DRAWINGS

Some embodiments are illustrated by way of example and not limitation in the figures of the accompanying drawings in which.

DETAILED DESCRIPTION

A spinal plate with compression locking and a method of fixating vertebrae using the spinal plate with compression locking are disclosed. In the following description, for the purposes of explanation, numerous specific details are set forth in order to provide a thorough understanding of example embodiments. It will be evident, however, to one skilled in the art, that an example embodiment can be practiced without all of the disclosed specific details.

Figure 1:
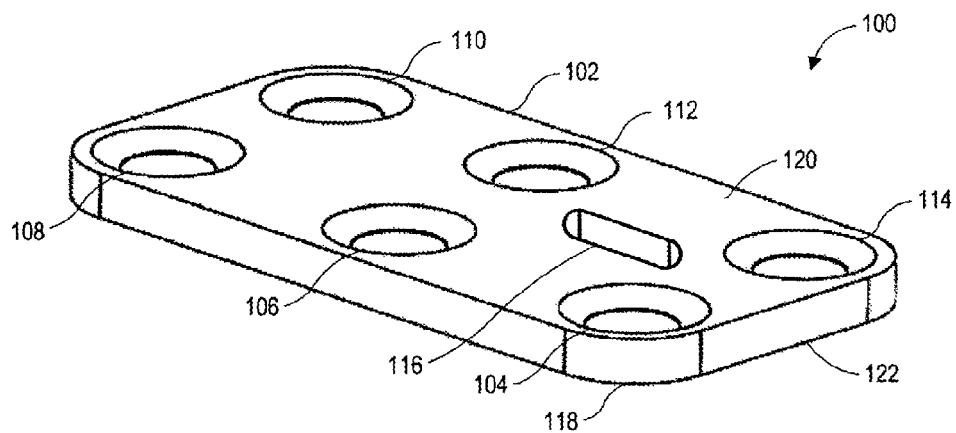
FIG. 1 illustrates a perspective view of an example spinal plate.

FIG. 1 illustrates a perspective view of an example spinal plate 100. The spinal plate 100 includes a plate body 102 and a plurality of screw-receiving openings (openings) 104-114 through the plate body 102. In some embodiments, the plate body 102 can also include at least one opening 116.

The plate body 102 can be made of a metal (e.g., titanium, stainless steel, or other metal), polyethylethylketone (PEEK), ceramic material, bio-absorbable material, other medically-surgically acceptable material, and combinations of these and/or conventional or later-developed materials that are resilient yet durable to withstand movement of the vertebrae.

The plate body 102 can be generally rectangular with planar top and bottom surfaces 120, 122 and rounded corners 118. The plate body 102 has a length, width and height. The dimensions of the plate body 102 depend generally on the region of the spine (e.g., cervical, thoracic, lumbar) as well as the number of vertebrae being fixated. As an example for a cervical application, the plate body 102 can be about 2 mm-to about 4 mm tall; about 15 mm wide; and between about 18 mm-about 70 mm long (depending on the number of vertebrae being fixated). To fixate two (2) vertebra, the length for of the plate body 102 can be about 18 mm-about 20 mm.

The plate body 102 can have a non-rectangular (e.g., irregular) shape. The top and bottom surfaces 120, 122 can also be non-planar (e.g., arcuate), as may be desirable for different spinal regions, anatomies and/or certain spinal procedures. For example, the plate body 102 can have a bone/barbell shape (e.g., wider at ends and narrower in center) and a variety of other shapes.

The plate body 102 is configured to be disposed along and to fixate a spinal segment (including a plurality of vertebrae) of the cervical, thoracic or lumbar region of the spinal column (not shown). The plate body 102 can be disposed about the anterior or lateral aspect of the spinal segment. Accordingly, the plate body 102 can have a variety of shapes, dimensions and surface curvatures to accommodate different spinal segments and aspects along the spinal column.

Figure 4:
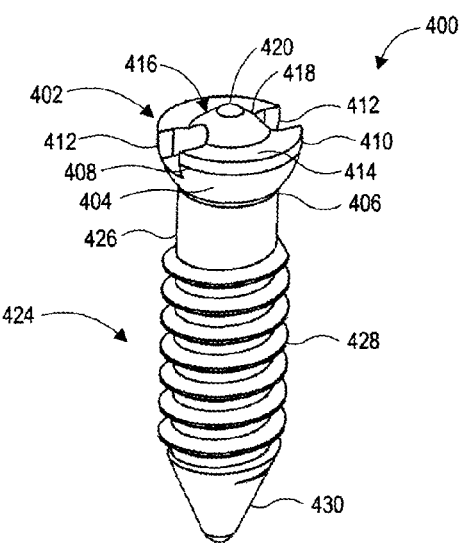
FIG. 4 illustrates a perspective view of a vertebral screw (screw)

The openings 104-114 are generally configured to receive vertebral screws (screws), such as screw 400 illustrated in FIG. 4, (or other screws 1900, 2306 described herein) in one or more trajectories through the plate body 102, securing the plate 100 to the spinal segment in order to fixate the vertebrae of the spinal segment. The locations of the openings 104-114 are shown as examples and openings 104-114 can be disposed at one or more locations about the plate body 102 required for particular spinal segments and/or spinal procedures. The openings 104-114 can also be biased through the plate body 102 toward a central axis of the plate body 102 to match different curvatures of spinal segment to be fixated.

Furthermore, the number, dimension and orientation of the openings 104-114 are given as examples. More or fewer openings of the same or different dimensions and orientations can be provided as required for fixation of certain spinal segments in the spinal column. In some embodiments, two openings can be provided, while in other embodiments, more than two openings can be provided, such as openings 104-114 shown in FIG. 1.

The at least one opening 116 is configured to enable viewing of at least one of the vertebrae in the spinal segment to be fixated. The dimension and location of the opening 116 through the plate body 102 are shown as an example. One or more similar or different openings 116 can be provided at one or more locations of the plate body 102. In some embodiments, the at least one opening 116 is made as open as possible but does not affect the structural stability or strength of the plate body 102. In some embodiments, the at least one opening 116 is not provided.

Figure 2:
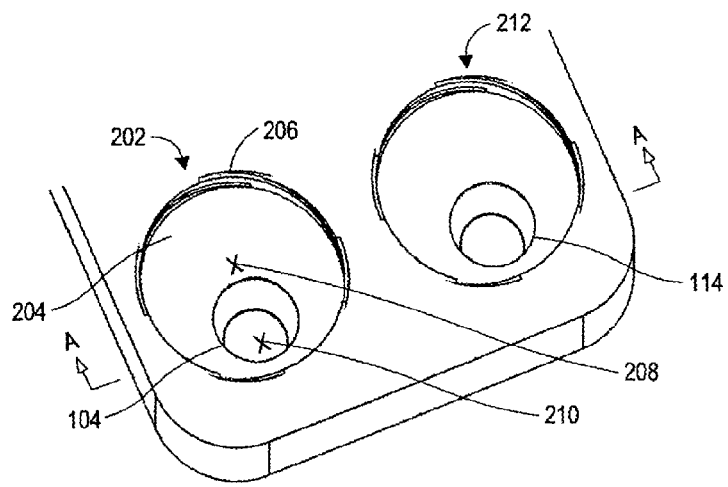
FIG. 2 illustrates perspective view of an example threaded recess provided in the plate body of the spinal that is eccentric (off-center) with reference to an opening of the plate body.

FIG. 2 illustrates a perspective view of an example threaded recess 202 provided in the plate body 102 that is eccentric (off-center) with reference to the opening 104. The recess 202 has a center 208, seat 204 and threading 206.

Whereas the opening 104 extends through the plate body 102, the recess 202 extends partially into the plate body 102. The center 208 of the recess 202 is off-center (eccentric) with reference to the center 210 of the opening 104. Furthermore, the opening 104 is encompassed entirely inside the recess 202.

In some embodiments, no point in the circumference of the opening 104 touches any other point in the circumference of the recess 202. In other embodiments, at least one point in the circumference of the opening 104 touches at least one point in the circumference of the recess 202. One or more other recesses can similarly be provided in the plate body 102 with reference to the other openings 106-114 of FIG. 1, such as a recess 212 illustrated in FIG. 2 with respect to opening 114.

The seat 204 is generally a planar surface below the top surface 120 and above the bottom surface 122 of the plate body 102. The seat 204 can be, but does not have to be, parallel to the top and bottom surfaces 120, 122 of the plate body 102. For example, the top and bottom surfaces 120, 122 can be arcuate while the seat 204 can be planar. The seat 204 is configured to provide a final stop to a threaded cap 500, which is described in greater detail below with reference to FIGS. 5 and 6.

Figure 5:
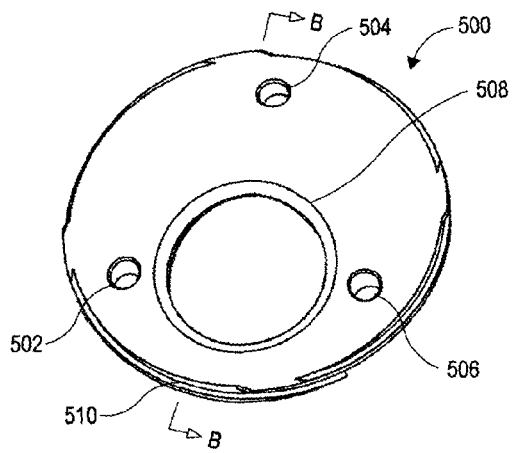
FIG. 5 illustrates a perspective top view of a threaded cap configured to be disposed in one or more alignment positions with respect to the threaded recess of FIG. 2.
Figure 6:
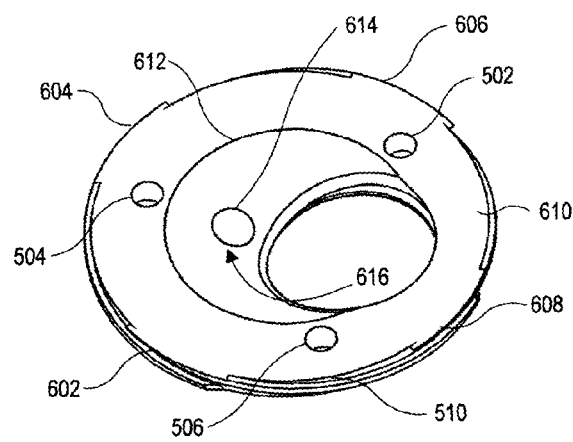
FIG. 6 illustrates a perspective bottom view of the threaded cap illustrated in FIG. 5.

The threading 206 is formed along the inner circumference of the recess 202 and is configured to threadably engage a threaded cap 500 of FIGS. 5 and 6, such that the cap 500 can be inserted (screwed) into and removed (unscrewed) from the recess 202. In some embodiments, the threading 206 can be configured for in-plane rotation, such that the cap 500 can rotate in-plane about the recess 202. The seat 204 provides the inner-most extent to which the threaded cap 500 can be inserted in the recess 202.

The threading 206 (lead, form and other thread factors) is configured such that any possible motion (wobble) of the screw 400 in the opening 104 is less likely to be converted to rotary motion, further mitigating the possibility of the threaded cap 400 from being unscrewed from the thread 206 of the recess 202.

Figure 3:
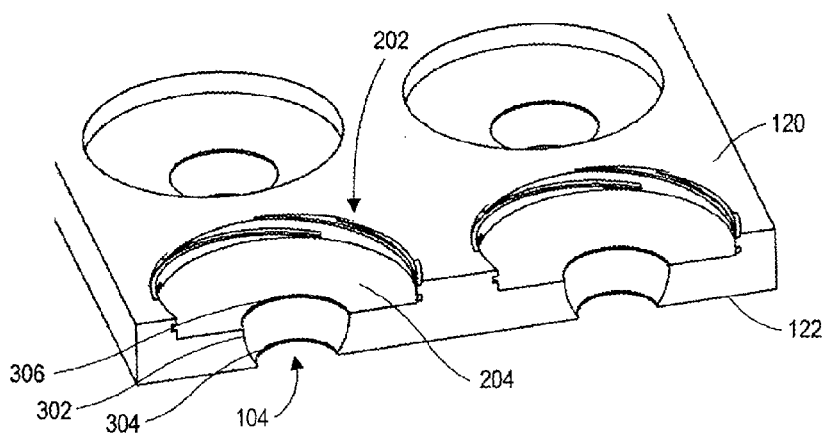
FIG. 3 illustrates a cross-sectional view of the plate body illustrated in FIG. 2.

FIG. 3 illustrates a cross-sectional view of the plate body 102 along plane A-A as illustrated in FIG. 2. Opening 104 is configured to secure the screw 400 of FIG. 4 in one or more trajectories through the plate body 102.

The opening 104 is generally defined by a sphere 302 that is truncated by a first diameter 304 along the bottom surface 122 of the plate body 102 and a second diameter 306 along the seat 204 of the recess 202. The first diameter 304 is smaller than the second diameter 306.

The opening 104 is generally configured to have a matching configuration to a screw 400 that will described in greater detailed below with reference to FIG. 4 (or any other screw described herein, such as screw 1900 or 2306). Accordingly, the opening 104 is configured to receive a similarly configured head 402 of the screw 400 in one or more trajectories through the plate body 102.

FIG. 4 illustrates a perspective view of a vertebral screw (screw) 400.

The screw 400 is a poly-axial screw that is configured to secure the spinal plate 100 to a vertebra of a spinal segment through the opening 104 of the plate body 102 in one or more trajectories. One or more additional screws 400 can be used to the secure the spinal plate to same or different vertebrae through openings 106-114 in the plate body 102 of the spinal plate 100.

The screw 400 can be made of a metal (e.g., titanium, stainless steel, other metal or metal alloys), polyethylethylketone (PEEK), ceramic material, bio-absorbable material, other medically-surgically acceptable material, and combinations of these and/or conventional or later-developed suitable materials that are resilient yet durable to withstand movement of the vertebrae.

The screw 400 includes a head 402 and body 424. The head 402 is defined by a sphere 404 that is truncated by a first diameter 406 and second diameter 408. The first diameter 406 is smaller than the second diameter 408, and the second diameter 408 is smaller than the diameter of the sphere 404 (not shown) that defines the head 402. The head 402 is further defined by a cylinder 410 that extends from the truncated sphere 404 to a top surface 414. The height of the cylinder 410 is within or circumscribed by the shape of the sphere 404, such that the head can pivot in the opening 104.

The head 402 of the screw 400 includes an engagement surface 416 and a plurality of recesses 412. The head 402 is configured to be disposed in the opening 104 in one or more trajectories with respect to the seat 204. More specifically, because of the matching configuration of the head 402 to the opening 104, the head 402 can be pivoted and rotated in the opening 104.

Accordingly, the geometry of the head 402 is configured similarly to the geometry of the opening 104, enabling the head 402 of the screw 400 to pivot and rotate in the opening 104 and to be secured in the opening 104 (as well as other openings 106-114) of the plate body 102 in one or more trajectories. The top surface 414 is configured to be approximately planar with seat 204 when the head 402 is disposed in the opening 104 approximately transversely to the seat 204.

In some embodiments, the truncated sphere 404 can be defined by the diameters 406, 408 such that the top surface 414 of the head 402 is below the seat 204 when the head 402 is disposed in the opening 104 approximately transversely to the seat 204. Disposing the top surface 414 of the head 402 below the seat 204 can provide a greater number of trajectories through the openings 104.

The engagement surface 416 is arcuate and extends approximately centrally above the top surface 414. The engagement surface 416 is configured to approximate a center of the sphere 404 that defines the head 402. The engagement surface 416 is further configured to engage the threaded cap 600 of FIGS. 5 and 6 such that the screw head 402 is pressed via approximately its center into at least a portion of the opening 104 to secure the screw 400 with respect to the spinal plate 100 in a selected trajectory.

In some embodiments illustrated in FIG. 4, the engagement surface 416 can be defined by the intersection of a truncated cone 418 and sphere 420, such that a continuous arcuate surface 416 is formed centrally on the top surface 414. The cone 418 is disposed between the surface 414 and the sphere 420. The engagement surface 416 (via center of sphere 420) approximates the center of the sphere 404.

The dimensions of the cone 418 and sphere 420 can be selected such that the centers of the spheres 404, 420 are approximately concentric, e.g., the center of sphere 420 approximates the center of the sphere 404. Accordingly, the screw head 402 (sphere 404) can be pressed through approximately its center via the center of sphere 420 into at least a portion of the opening 104 to secure the screw 400 with respect to the spinal plate 100 in a selected trajectory. The sphere 420 can be any dimension such that its center is approximately concentrically disposed in relation to the center of the sphere 404.

In other embodiments, the engagement surface 416 can be defined by one or more shapes, such as cylindrical, conical, spherical and/or other shapes. For example, the cone 418 and sphere 420 can be substituted with a centrally disposed sphere (e.g., hemisphere or another truncated portion of a sphere) the center of which is concentric with the center of sphere 404, such that the sphere 404 can be pressed approximately via its center.

The recesses 412 are configured to engage reciprocal extensions of a driving tool (not shown) that can be used to drive (rotate) the screw 400 into a vertebra of the spinal segment to be engaged. The recesses 412 can be disposed at various locations about the periphery of the top surface 414. In some embodiments as illustrated in FIG. 4, two recesses 412 are disposed on opposite sides of the engagement surface 416, e.g., approximately 180 degrees with respect to one another. In other embodiments, more than two recesses—which are equidistantly or variously spaced about the periphery of the top surface 414—can be provided.

The body 424 of the screw 400 includes a shaft 426, thread 428 and tip 430. The thread 428 is provided along a portion of the shaft 426 below the head 402, such that the screw 400 can be disposed in the opening 104 of the plate body 102 in a plurality of trajectories and such that the screw 400 can engage the vertebra. The tip 430 is configured to enable the screw 400 to penetrate the vertebra. The thread 428 and tip 430 can be self-cutting and/or the vertebra can be pre-drilled.

FIG. 5 illustrates a perspective top view of a threaded cap 500 that is configured to be disposed in one or more alignment positions with respect to the recess 202 of FIG. 2.

The threaded cap 500 can be made of a metal (e.g., titanium, stainless steel, other metal or metal alloys), polyethylethylketone (PEEK), ceramic material, bio-absorbable material, other medically-surgically acceptable material, and combinations of these and/or conventional or later-developed suitable materials that are resilient yet durable to withstand movement of the vertebrae. The threaded cap 500 includes openings 502-506, alignment opening 508 and threading 510.

The openings 502-506 are configured to engage respective extensions of a tool (e.g., prong screw driver) to threadably engage the threading 510 of the threaded cap 500 with the threading 206 of the recess 202, and further to rotate the threaded cap 500 in the recess 202 between a screw-loading alignment and a screw-compression alignment. Instead of the openings 502-506, a different engagement mechanism can be used to engage threading 510 of threaded cap 500 with threading 206 of the opening 202.

In the screw-loading alignment, the alignment opening 508 approximates the opening 104, enabling the receipt of the screw 400 through the threaded cap 500 into the opening 104, pivoting of the head 402 of the screw 400 in the opening 104 into a selected trajectory, and rotation (threading) of the screw 400 into a vertebra through the threaded cap 500 in the selected trajectory. Because of the matching configuration of the head 402 and the opening 104 and the alignment of the opening 104 and the opening 508, the screw 400 can be threaded into the vertebra through the plate body 102 of the spinal plate 100 in one of many trajectories, as may be advantageous in order to achieve better engagement with the vertebra.

FIG. 6 illustrates a perspective bottom view of the threaded cap 500 illustrated in FIG. 5.

The threaded cap 500 further includes thread extensions (starts) 602-608, planar bottom surface 610, compression ramp 612, and recess (detent) 614.

The thread extensions 602-608 are a part (starts) of the threading 510 and are disposed about the circumference of the threaded cap 500. The thread extensions 602-608 are sized and dimensioned to be received in respective alignment slots 802-808, which will be described in greater detail below with reference to FIG. 8. Further, the extensions 602-608 are configured to enable engagement of threading 510 of threaded cap 500 with threading 206 of the recess 202, such that the threaded cap 500 can screw into the recess 202 via the threading 206. In some embodiments, more or fewer extensions (starts) in the threaded cap 500 and respective alignment slots in the recess 202 can be provided. For example, three extensions and alignment slots can be provided.

In some embodiments, the bottom surface 610 can mate in a planar configuration with the seat 204 of the recess 202.

The compression ramp 612 is configured to approximate and progressively compresses or engage the engagement surface 416 of the screw 400 into the opening 104, as the threaded cap 500 rotates along engagement path 616 between the screw-loading alignment and the screw-compression alignment in the recess 202.

The recess (detent) 614 approximates the engagement surface 416 and is configured to receive at least a portion of the engagement surface 416 in a compression engagement with respect to the opening 104. In some embodiments, the recess 614 is configured to accommodate at least a portion of the sphere 420 of the engagement surface 416. The recess 614 can provide a clicking that indicates successful compression engagement. Further, the recess 614 mitigates any possible motion (wobble) of the head 402 of screw 400 in the opening 104 and about engagement surface 612, such that it is less likely that such motion is converted to rotary motion that can unscrew the threaded cap 500 from the recess 202.

Figure 7:
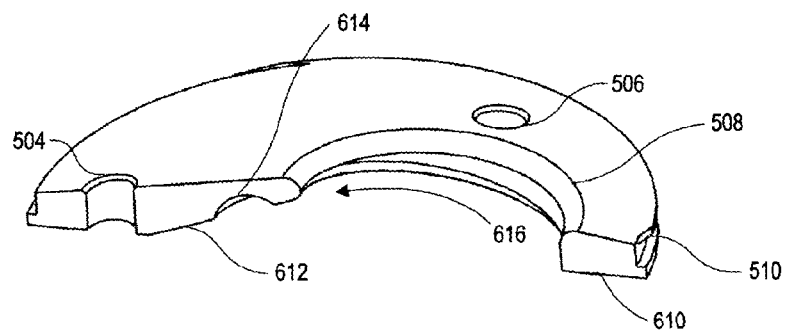
FIG. 7 illustrates a cross-sectional view of the threaded cap illustrated in FIG. 5.

FIG. 7 illustrates a cross-sectional view of the threaded cap 500 along plane B-B illustrated in FIG. 5.

The compression ramp 612 is a chamfered surface with respect to the bottom surface 610 along the engagement path 616 that the engagement surface 416 of the screw 400 follows as the threaded cap 500 is rotated in the recess 202. As the threaded cap 500 is rotated into the screw-compression alignment, the recess (detent) 614 engages the engagement surface 416 of the screw 400 or a portion thereof.

Figure 8:
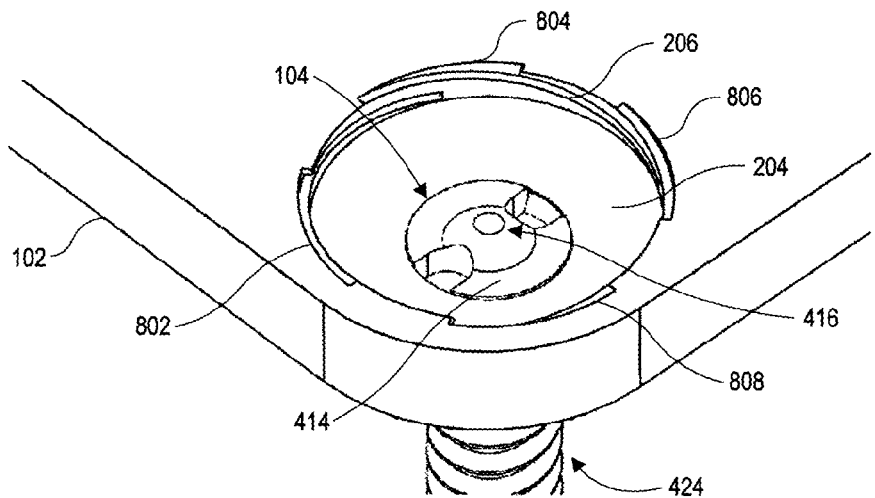
FIG. 8 illustrates a perspective view of the screw of FIG. 4 disposed in the opening of the plate body in the spinal plate of FIG. 1.

FIG. 8 illustrates a perspective view of the screw 400 of FIG. 4 disposed in the opening 104 of the plate body 102 in the spinal plate 100 of FIG. 1.

It is noted that the screw 400 is shown in the opening 104 to illustrate the interface of these elements. However, it is intended that the screw 400 will inserted and threaded into a vertebra through the threaded cap 500 of FIGS. 5 and 6, as will be described in greater detail below with reference to FIGS. 9 and 10.

The threading 206 of the recess 202 is configured to include thread alignment (engagement) slots 802-808. The thread alignment slots 802-808 of the recess 202 are configured to receive reciprocal thread extensions 602-608 of the threaded cap 500, such that the threaded cap 500 can be received in alignment with respect to the recess 202. Mores specifically, the foregoing slots/extensions enable precise alignment of the threaded cap 500 and the recess 202 into a screw-loading alignment and screw-compression alignment. The alignment slots 802-808 represent respective starts to the threading 206 of the recess 202. The number and configuration of the alignment slots 802-808 can be adjusted based on the respective number and configuration of the thread extensions 602-608.

As particularly illustrated in FIG. 8, the screw head 402 of the screw 400 is seated into the opening 104 of the plate body 102 in a generally vertical (transverse) trajectory, such that the planar surface 414 approximates the planar seat 204. Other trajectories of the screw 400 through the opening 104 of the plate body 102 are of course possible. Because of matching spherical configuration of the head 402 of the screw 400 and the opening 104 of the spinal plate 100, the screw 400 can pivot in the various trajectories through the spinal plate 100 via the opening 104. Accordingly, in various trajectories, the engagement surface 416 extends into the recess 202 above the seat 204.

Figure 9:
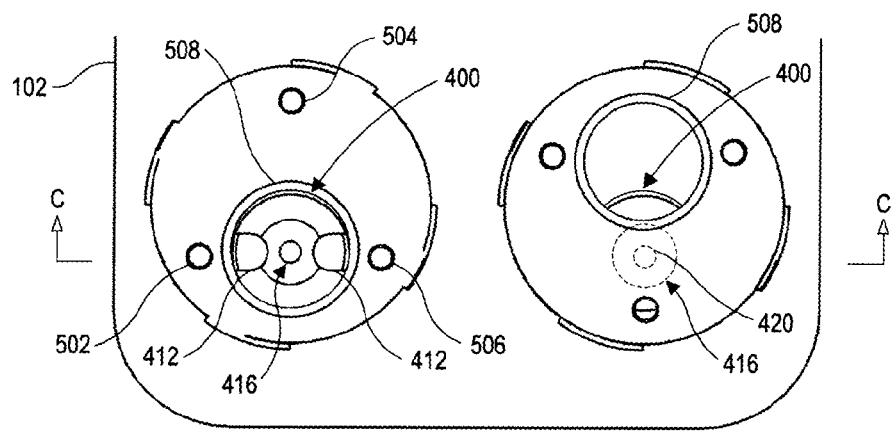
FIG. 9 illustrates a perspective view of the threaded cap of FIG. 5 engaging threading of the threaded recess in a screw-loading alignment and in a screw-compression alignment.

FIG. 9 illustrates a perspective view of a threaded cap 500 engaging threading 206 of the recess 202 in a screw-loading alignment and in a screw-compression alignment.

The extensions 602-608 of the threaded cap 500 have been received via respective alignment slots 802-808 into the recess 202. Furthermore, the threaded cap 500 has been rotated at least partially (e.g., clockwise) via the openings 502-506 to engage the threading 510 with the threading 206 and to align the alignment opening 508 of the threaded cap 500 with the opening 104 of the plate body 102 in the screw-loading alignment.

It is to be noted that the spinal plate 100 with the threaded cap 500 engaging the recess 202 in the screw-loading alignment is inserted into position with respect to the vertebrae of spinal segment to be fixated via the spinal plate 100. Additional caps 500 in relation to one or more of the openings 106-114 are also engaged in screw-loading alignment before insertion into position with respect to the spinal segment to be fixated. In alternate embodiments, the spinal plate 100 and threaded cap 500 can be inserted separately.

In the screw-loading alignment, the alignment opening 508 allows receipt of the screw 400 through the threaded cap 500 into the opening 104, pivoting of the head 402 of the screw 400 in the opening 104 into a selected trajectory, and rotation of the body 424 of the screw 400 into the vertebra in the selected trajectory through the threaded cap 500 via recesses 412. Because of the matching configuration of the screw head 402 and the opening 104, the screw 400 can be threaded into a vertebra of the spinal segment through the plate body 102 in one of many trajectories, as may be advantageous in order to achieve better engagement with the vertebra.

Once the body 424 of the screw 400 has engaged the vertebra securely through opening 104, the head 402 of the screw engages at least a portion of the opening 104 of the plate body 102. Thereafter, the threaded cap 500 is threaded in the recess 202 from the screw-loading alignment into a screw-compression alignment. The rotation of the threaded cap 500 progressively compresses the head 402 of the screw 400 via engagement surface 416 into the opening 104 of the plate body 102 in the selected trajectory.

More specifically, the compression ramp 612 progressively compresses the head 402 along the engagement path 616 into the opening 104 until the recess (detent) 614 engages the engagement surface 416 (or a portion thereof) of the screw head 402 in the screw-compression alignment. The recess 614 also compresses the engagement surface 416 of the screw head 402 in the screw-compression alignment. Generally, the screw-compression alignment can be approximately up to 180 degrees or less with respect to the screw-loading alignment. Other alignments between loading and compression can be used.

In the screw-compression alignment, the threaded cap 500 engages the engagement surface 416 (or a portion thereof) of the head 402 of the screw 400 via recess 614, compressing the screw head 402 (sphere 404) of the screw 400 into the engaged portion of the opening 104 in the selected trajectory via the sphere 420 of the engagement surface 416. This mitigates the wobbling of poly-axial screws in the openings of prior art spinal plates. The screw 400 does not wobble in the opening 104 if and when the body 424 of the screw 400 loosens with respect to the vertebra. Similarly, the body 424 of the screw 400 is also less likely to loosen with respect to the vertebra because the screw 400 does not wobble in the opening 104. Accordingly, rigid fixation can be provided across the vertebrae.

Figure 10:
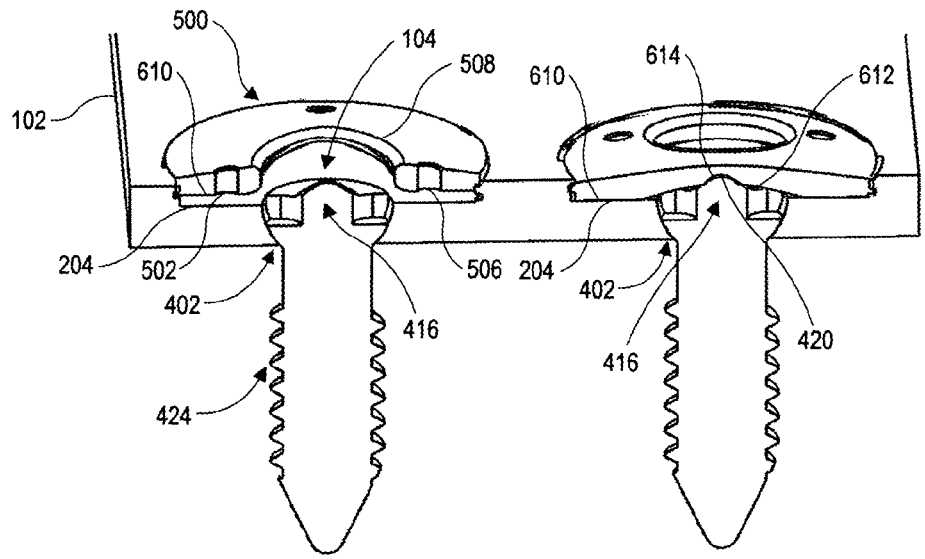
FIG. 10 illustrates a cross-sectional view of the threaded cap of FIG. 5, engaging threading of the threaded recess in the screw-loading alignment and in the screw-compression alignment.

FIG. 10 illustrates a cross-sectional view of a threaded cap 500 along plane C-C in FIG. 9, engaging threading 206 of recess 202 in the screw-loading alignment and in the screw-compression alignment.

In the screw-loading alignment, the threaded cap 500 has been advanced (threaded) partially into the recess 202 to align opening 508 with the opening 104, such that the screw 400 can be received through the opening 508 into the opening 104. The bottom surface 610 of the threaded cap 500 is disposed at a first distance to the seat 204.

The screw 400 is received through the aligned opening 508 of the threaded cap 500 and the opening 104. A trajectory for the screw 400 in relation to a vertebra is selected and the screw 400 is threaded into the vertebra to secure the plate 100 to the vertebra via the opening 104. The screw head 402 of the screw 400 engages at least a portion of the opening 104 in the selected trajectory.

Thereafter, the threaded cap 500 is advanced further in the recess 202 into the screw-compression alignment in which the threaded cap 500 engages the engagement surface 416 (sphere 420) of the head 402 via recess 614, compressing the screw head 402 (sphere 404) of the screw 400 into the engaged portion of the opening 104 in the selected trajectory via sphere 420 of the engagement surface 416. This compression reduces or eliminates the wobbling of the screw 400 in the opening 104 if and when the screw 400 loosens with respect to the vertebra and also reduces the likelihood that the screw will loosen with respect to the vertebra.

In the screw-compression alignment, the bottom surface 610 of the threaded cap 600 can engage the seat 204, providing friction across the engaging surfaces 204, 610 to further counteract any unscrewing forces that can compel the threaded cap 500 from the recess 202. In other embodiments, the bottom surface 610 of the threaded cap 500 is at second distance to the seat 204. The second distance of the screw-compression alignment is smaller than the first distance of the screw-loading alignment.

Figure 11:
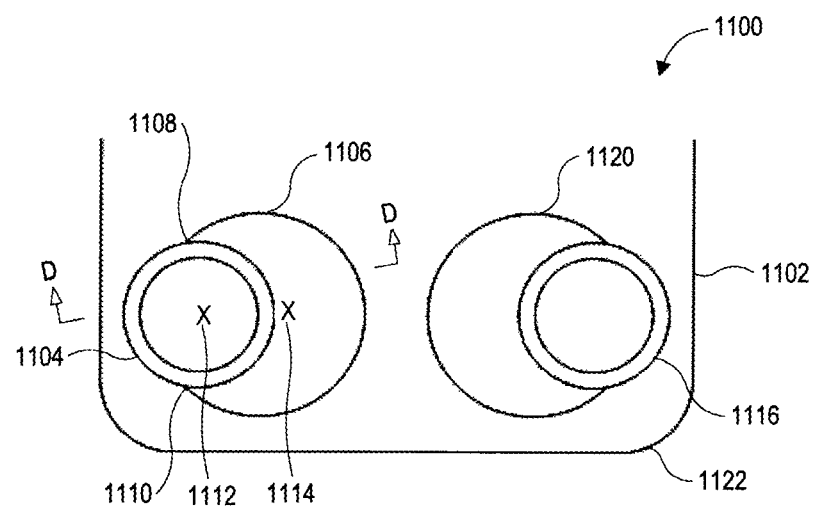
FIG. 11 illustrates a perspective view of an example spinal plate.

FIG. 11 illustrates perspective view of an example spinal plate 1100.

The spinal plate 1100 includes a plate body 1102, plurality of openings 1104, 1116 through plate body 1102 and associated plurality of threaded recesses 1106, 1120. In some embodiments, the spinal plate 1100 can also include at least one opening through plate body 102 (not shown in FIG. 11) configured to enable viewing of at least one of the vertebrae in the spinal segment to be fixated such as opening 116 described with reference to FIG. 1. Although only several openings 1104, 1116 and associated recesses 1106, 1120 are illustrated in FIG. 11, it should be noted that multiple openings and associated recesses can be provided to fixate multiple vertebrae of the spinal segment.

The plate body 1102 can be made of a metal (e.g., titanium, stainless steel, or other metal), polyethylethylketone (PEEK), ceramic material, bio-absorbable material, other medically-surgically acceptable material, and combinations of these and/or conventional or later-developed suitable materials that are resilient yet durable to withstand movement of the vertebrae.

The plate body 1102 is generally rectangular with planar top and bottom surfaces 1202, 1204 (illustrated in FIG. 12) and rounded corners 1122. The plate body 1102 has a length, width and height, which can be similar to or different than described with reference to the plate body 102 of FIG. 1. The plate body 1102 can have a non-rectangular (e.g., irregular) shape. The top and bottom surfaces 1202, 1204 can also be non-planar (e.g., arcuate), as may be desirable for certain regions of the spine or spinal procedures.

The plate body 1102 is configured to be disposed along and to fixate a spinal segment (including a plurality of vertebrae) of the cervical, thoracic or lumbar region of the spinal column (not shown). The plate body 1102 can be disposed about the anterior or lateral aspect of the spinal segment. Accordingly, the plate body 1102 can have a variety of shapes, dimensions and surface curvatures to accommodate different spinal segments and aspects along the spinal column. The shapes, dimensions and configurations of the plate body 1102 can be similar to or different than described with reference to the plate body 102 of FIG. 1.

The openings 1104, 1116 (and/or other similar openings) are generally configured to receive vertebral screws (screws) 400 of FIG. 4 (or other screws such as, screws 1900 or 2306), in one or more trajectories through the plate body 1102, securing the plate 1100 to the spinal segment in order to fixate the vertebrae of the spinal segment. The locations of the openings 1104, 1116 are shown as examples and these and/or other openings can be disposed at one or more locations about the plate body 1102 required for particular spinal segments and/or spinal procedures.

The threaded recesses 1106, 1120 of plate 1100 are eccentric (off-center) with reference to their associated openings 1104, 1116, respectively, as described below. For simplicity and to facilitate understanding of the subject matter disclosed herein, only the representative opening 1104 and associated threaded recess 1106 will be described in greater detail below with reference to FIGS. 11-18. It is understood that the other openings (e.g., opening 1116 and/or other openings) and associated recesses (e.g., recess 1120 and/or other recesses) are configured similarly to the representative opening 1104 and associated recess 1116 described below.

The opening 1104 has a center 1112 and the recess 1106 has a center 1114. The centers 1112, 1114 are off-center (eccentric). Further, the recess 1106 intersects the opening 1104 at points 1108, 1110, such that only a portion of the opening 1104 is encompassed inside the recess 1106. Furthermore, the intersection is such that the center 1112 of the opening 1104 is encompassed in the recess 1106.

Figure 12:
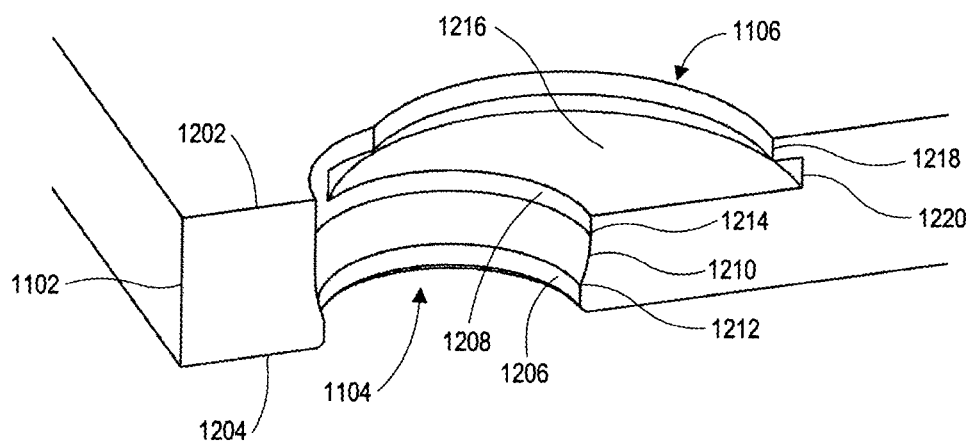
FIG. 12 illustrates a cross-sectional view of an opening and a recess of the spinal plate illustrated in FIG. 11.

FIG. 12 illustrates a cross-sectional view of the opening 1104 and recess 1106 of spinal plate 1100 along plane D-D illustrated in FIG. 11.

The opening 1104 is generally defined by cylindrical openings 1206, 1208 and spherical opening 1210 that is disposed between the openings 1206, 1208.

Specifically, the first cylindrical opening 1206 has a first diameter 1212 and a first height. The first opening 1206 extends through and from the bottom surface 1204 partially into the plate body 1102. The second cylindrical opening 1208 has a second diameter 1214 and a second height. The second opening 1206 extends through and from a seat 1216 partially into the plate body 1102. The first and second height can be the same.

The spherical opening 1210—disposed between openings 1206, 1208—is defined by a sphere 1210 that is truncated by the first diameter 1212 and the second diameter 1214. The first diameter 1212 is smaller than the second diameter 1214. The spherical opening 1210—defined as diameters 1212, 1214—approximates the sphere 404 defined by diameters 406, 408 of the head 402 in the screw 400 illustrated in FIG. 4.

The opening 1104 (via spherical opening 1210) has an approximate matching configuration to the head 402 of the screw 400. Furthermore, the heights of the openings 1206, 1208 can approximate the height of a cylinder 410 of the screw head 402. Accordingly, the head 402 can pivot in the opening 1104 such that at least a portion of the engagement surface 416 of the screw head 402 extends into the recess 1106.

The recess 1106 includes a seat 1214, extension 1218 and channel 1220. The seat 1214 is generally a planar surface below the top surface 1202 and above the bottom surface 1204 of the plate body 1102 of the spinal plate 1100. The seat 1214 can be, but does not have to be, parallel to the top and bottom surfaces 1202, 1204 of the plate body 1102. As will be described in greater detail with reference to FIGS. 15-18, the seat 1412 is configured to receive a crescent-shaped cap 1300 of FIG. 13 in a generally planar configuration.

The extension 1218 and channel 1220 extend about the periphery of the recess 1106, except for a portion of the periphery eliminated as a result of the intersection of the opening 1104 with the recess 1106.

The extension 1218 is generally planar with the top surface 1202 of the plate body 1102. The extension 1218 overhangs the recess 1106, forming the channel 1220 that extends between the seat 1214 and the extension 1218. The channel 1220 is configured to receive a lip 1302 of the crescent-shaped cap 1300 of FIG. 13, while the extension 1218 is configured to movably engage the lip 1302 such that the crescent-shaped cap 1300 is rotationally engaged and retained in the recess 1106.

Figure 13:
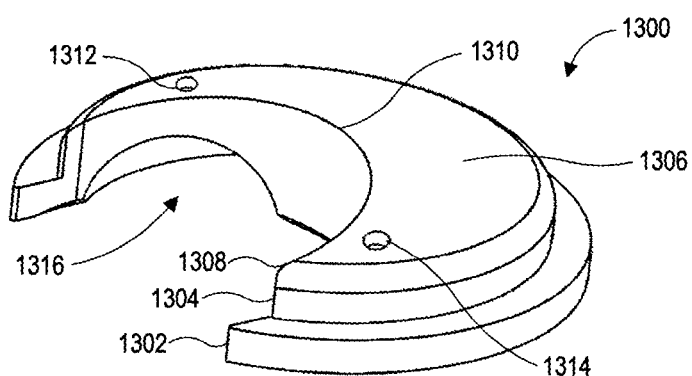
FIG. 13 illustrates perspective view of the example crescent-shaped cap.

FIG. 13 illustrates perspective view of the example crescent-shaped cap 1300. The crescent-shaped cap 1300 includes a lip 1302, wall 1304, top surface 1306, chamfer 1308, alignment opening 1310, and compression ramp 1316.

The shape of the crescent-shaped cap 1300 is defined by an alignment opening 1310 that approximates the opening 1104. The lip 1302 is configured to engage extension 1218 of the recess 1106. More specifically, the lip 1302 is generally planar and is configured to be disposed in a generally planar configuration in the seat 1216 such that the lip 1302 can rotate in the channel 11220 of the recess 1106. The wall 1304 extends generally upwardly from the lip 1302 to the top surface 1306. The chamfer 1308 smoothes the intersection or transition between the wall 1304 and top surface 1306.

In some embodiments, the crescent-shaped cap 1300 can be rotated in the recess 1106 via a tool (not shown) that engages the opening 1302 and the wall 1304. In other embodiments, openings 1312, 1314 can be provided. The openings 1312, 1314 are configured to engage respective extensions of a tool (e.g., prong screw driver) to rotate the crescent-shaped cap 1300 in the recess 1106. Alternate engagement mechanism(s) can also be provided to rotate the crescent-shaped cap 1300 in the recess 1106.

The crescent-shaped cap 1300 can be rotated about the recess 1106 between a screw-loading alignment and a screw-compression alignment. In the screw-loading alignment, the alignment opening 1310 approximates the opening 1104. The configuration of the compression ramp 1316 approximates the engagement surface 416 of the screw 400 (or other screw, such as screw 1900 or 2306). The compression ramp 1316 is configured to progressively compress or engage the engagement surface 416 of the screw 400 as the crescent-shaped cap 1300 rotates between the screw-loading alignment and the screw-compression alignment. The compression ramp 1316 will be described in greater detail below with reference to FIG. 14.

Figure 14:
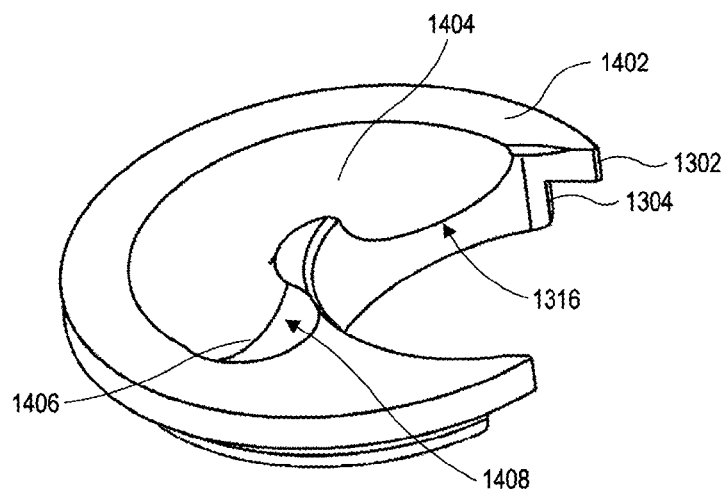
FIG. 14 illustrates a compression ramp of the crescent-shaped cap illustrated in FIG. 13.

FIG. 14 illustrates the compression ramp 1316 of the crescent-shaped cap 1300 of FIG. 13.

The bottom surface 1402 of the crescent-shaped cap 1300 is generally planar and is configured to mate in a planar configuration with the seat 1216 of the recess 1106, such that the crescent-shaped cap 1300 can be rotated about the recess 1106.

The compression ramp 1316 is configured to approximate and progressively compresses the engagement surface 416 of the screw 400 into the opening 1104, as the crescent-shaped cap 1300 rotates between the screw-loading alignment and the screw-compression alignment in the recess 1106.

The compression ramp 1316 includes a ramped surface 1404, ridge 1406 and a locking recess (detent) 1408. The ramped surface 1404 extends from the inner opening 1310 to the locking recess 1408, along a travel path of the engagement surface 416 about the crescent-shaped cap 1300, as the crescent-shaped cap 1300 rotates in the recess 1106 between the screw-loading alignment and the screw-compression alignment.

The ramped surface 1404 progressively provides more compression along the travel path, with the ridge 1406 providing the most compression of the compression ramp 1316. The locking recess 1408 is slightly less compressive than the ridge 1406, such that engagement surface 416 can be locked by the ridge 1406 in the locking recess 1408.

The locking recess 1408 approximates the engagement surface 416 and is configured to receive at least a portion of the engagement surface 416 in a compression engagement with respect to the opening 1104. In some embodiments, the locking recess 1408 is configured to accommodate at least a portion of the sphere 420 of the engagement surface 416. The recess 1408 can provide a clicking that indicates successful compression engagement. Further, the locking recess 1408 mitigates any possible motion (wobble) of the head 402 of screw 400 in the opening 1104, such that it is less likely that such motion is converted to rotary motion that can rotate the crescent-shaped cap 1300 from the screw-compression alignment to the screw-loading alignment.

Figure 15:
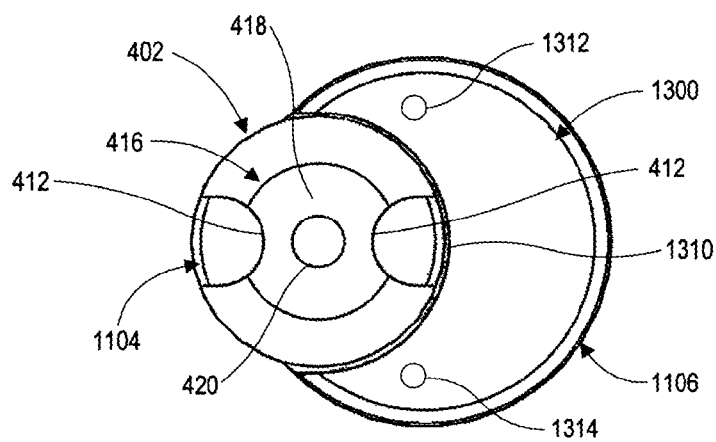
FIG. 15 illustrates a top view of the crescent-shaped cap engaging the recess of FIG. 12 in a screw-loading alignment.

FIG. 15 illustrates a top view of the crescent-shaped cap 1300 engaging the recess 1106 in a screw-loading alignment.

In the screw-loading alignment, the alignment opening 1310 in crescent-shaped cap 1300 approximates the opening 1104 in the plate body 1102, allowing receipt of the screw 400 into the opening 1104, pivoting of the head 402 of the screw 400 in the opening 1104 into a selected trajectory, and rotation of the body 424 of the screw 400 into the vertebra in the selected trajectory through the moon shaped cap 1300.

Because of the matching configuration of the screw head 402 and the opening 1104, the screw 400 can be received in the opening 1104 in one of many trajectories so that the vertebra can be engaged (threaded) in the trajectory that is advantageous for better engagement. Recesses 412 in the head 402 are used to thread the screw 400 into the vertebra.

Figure 16:
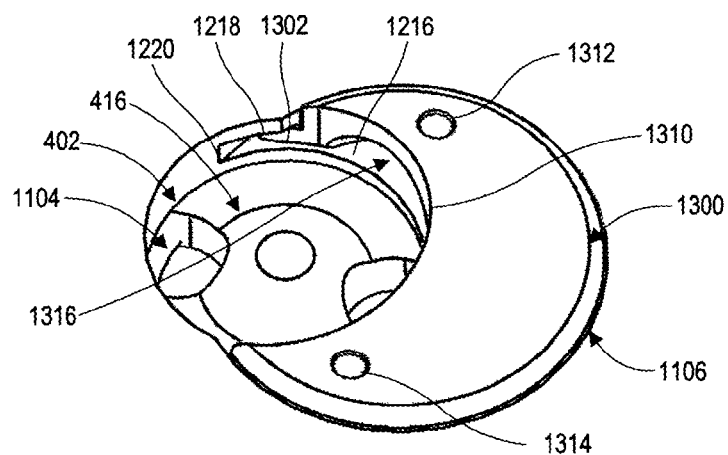
FIG. 16 illustrates perspective view of the crescent-shaped cap engaging the recess of FIG. 12 in the screw-loading alignment.

FIG. 16 illustrates perspective view of the example crescent-shaped cap 1300 engaging the recess 1106 of the spinal plate 1100 in the screw-loading alignment.

The bottom surface 1402 of the crescent-shaped cap 1300 is disposed in a planar configuration with the seat 1216 of the recess 1106. The crescent-shaped cap 1300 is secured in the recess 1106 by the lip 1302 that is disposed in the channel 1220 and engaged by the extension 1218, such that the crescent-shaped cap 1300 can be rotated about the recess 1106.

In the screw-loading alignment, the opening 1310 of the crescent-shaped cap 1300 approximates the opening 1104 in the plate body 1102 of the spinal plate 1100. The screw 400 has been inserted through the opening 1310 into the opening 1104. Furthermore, the screw 400 has been threaded via recesses 412 into the vertebra of the spinal segment in the selected trajectory. The head 402 of the screw 400 engages at least a portion of the opening 1104 of the plate body 1102.

The engagement surface 416 of the screw 400 extends at least partially into the recess 1106. The compression ramp 1316 at the inner opening 1310 generally approximates the extension of the engagement surface 416 into the recess 1106, such that compression ramp 1316 can easily slide over or engage the engagement surface 416.

Figure 17:
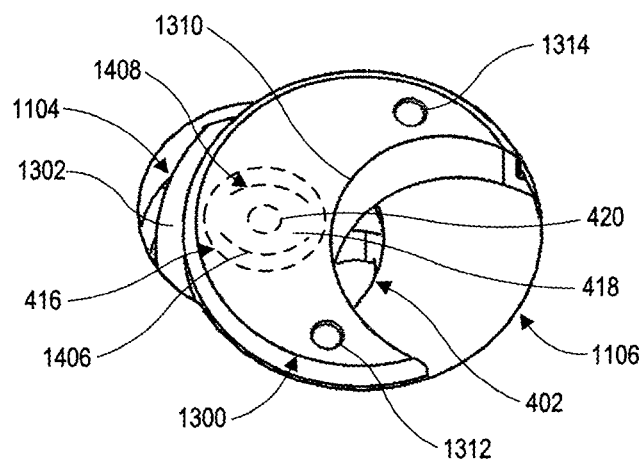
FIG. 17 illustrates a perspective view of the crescent-shaped cap engaging the recess of FIG. 12 in a screw-compression alignment.

FIG. 17 illustrates a perspective view of the crescent-shaped cap 1300 engaging the recess 1106 of the spinal plate 1100 in a screw-compression alignment.

Once the body 424 of the screw 400 has engaged the vertebra securely through opening 1104 in the selected trajectory, the head 402 of the screw 400 engages at least a portion of the opening 1104 in the plate body 1102 of the spinal plate 1100. The crescent-shaped cap 1300 is thereafter rotated in the recess 1106 from the screw-loading alignment into the screw-compression alignment. In the screw-compression alignment, the crescent-shaped cap 1300 covers a substantial portion of screw head 402.

The rotation of the crescent-shaped cap 1300 in the recess 1006 from the screw-loading alignment into the screw-compression alignment progressively compresses the head 402 of the screw 400 via engagement surface 416 into the engage portion of the opening 1104 of the plate body 102 in the selected trajectory.

More specifically, the ramped surface 1404 of the compression ramp 1316 progressively compresses the head 402 into the opening 1104 until the recess (detent) 1408 of the compression ramp engages at least a portion of the engagement surface 416. Generally, the screw-compression alignment can be up to 180 degrees or less with respect to the screw-loading alignment. In various embodiments, the alignment can be different between loading and compression.

Figure 18:
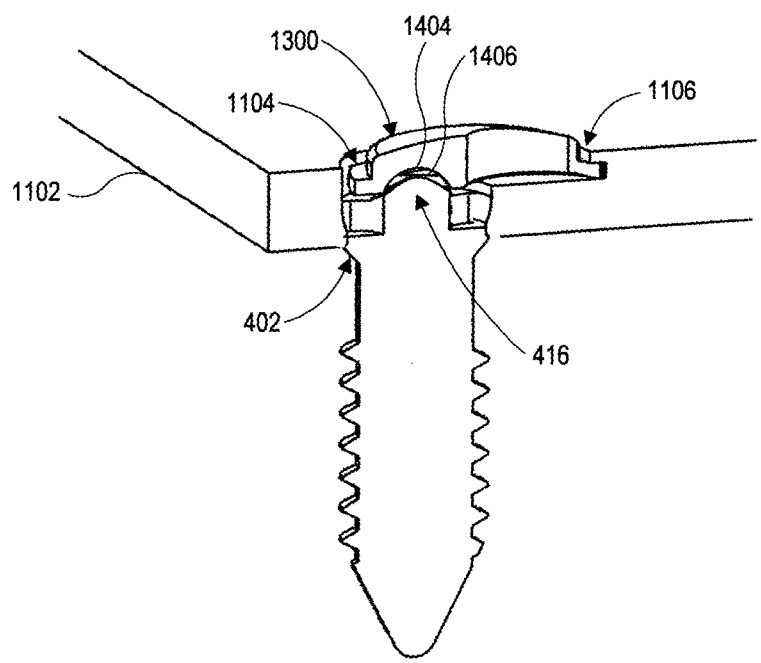
FIG. 18 illustrates a cross-sectional view of the example crescent-shaped cap between the screw-loading alignment and the screw-compression alignment with respect to the opening in the spinal plate of FIG. 11 and the screw of FIG. 4.

In the screw-compression alignment, the locking recess 1408 of compression ramp 1316 engages the engagement surface 416 (or a portion thereof) of the head 402 of the screw 400, compressing of the head 402 (sphere 404) of the screw 400 into the engaged portion of the opening 1104 in the selected trajectory via the sphere 420 of the engagement surface 416. This mitigates the wobbling of poly-axial screws in the openings of prior art spinal plates. The screw 400 does not wobble in the opening 1104 if and when the body 424 of the screw 400 loosens with respect to the vertebra. Similarly, the body 424 of the screw 400 is also less likely to loosen with respect to the vertebra because the screw 400 does not wobble in the opening 104. Accordingly, rigid fixation can be provided across the vertebrae FIG. 18 illustrates a cross-sectional view of the example crescent-shaped cap 1300 between the screw-loading alignment and the screw-compression alignment with respect to the opening 1104 in the plate body 1102 and screw 400.

The compression ramp 1316 of the crescent-shaped cap 1300 rides over the engagement surface 416 as the crescent-shaped cap 1300 is rotated in the recess 1106, with the ramped surface 1404 progressively increasing compression along its path and the ridge 1406 providing the most compression on the engagement surface 416 of the screw 400, until the locking recess 1408 (shown in FIG. 14) engages the engagement surface 416 past the ridge 1406.

The locking recess 1408 compresses the engagement surface 416 of the screw 400 in which compression of sphere 420 compresses the head 402 (sphere 404) of the screw 400—as the centers of spheres 420, 404 are approximately concentric—into the engaged portion of the opening 1104 in the selected trajectory.

Figure 19:
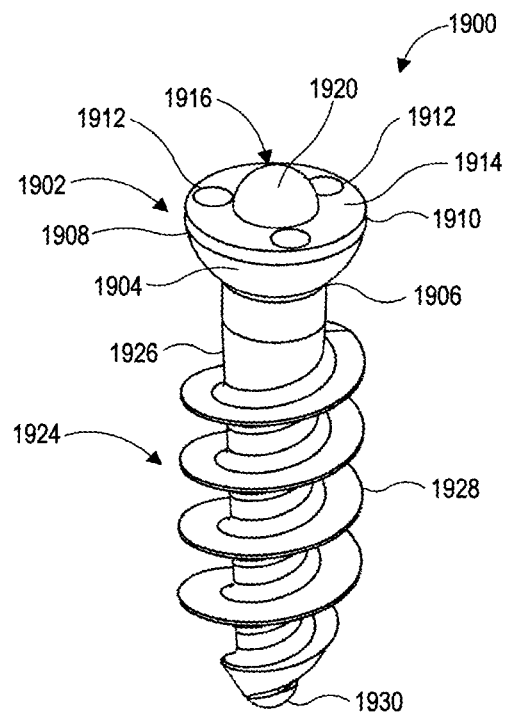
FIG. 19 illustrates a perspective view of a vertebral screw (screw)

FIG. 19 illustrates a perspective view of a vertebral screw (screw) 1900.

The screw 1900 is a poly-axial screw that is configured to secure the spinal plate 1100 to a vertebra of a spinal segment through the opening 1104 of the plate body 1102 in one or more trajectories. One or more additional screws 1900 can be used to the secure the spinal plate 1100 to same or different vertebrae through respective openings in the plate body 1102 of the spinal plate 1100.

The screw 1900 can be made of a metal (e.g., titanium, stainless steel, or other metal), polyethylethylketone (PEEK), ceramic material, bio-absorbable material, other medically-surgically acceptable material, and combinations of these and/or conventional or later-developed suitable materials that are resilient yet durable to withstand movement of the vertebrae.

The screw 1900 includes a head 1902 and body 1924. The head 1902 is defined by a sphere 1904 that is truncated by a first diameter 1906 and second diameter 1908. The first diameter 1906 is smaller than the second diameter 1908, and the second diameter 1908 is smaller than the diameter of the sphere 1904 (not shown) that defines the head 1902. The head 1902 is further defined by a cylinder 1910 that extends from the truncated sphere 1904 to a top surface 1914. The height of the cylinder 1910 is within or circumscribed by the shape of the sphere 1904.

The head 1902 of the screw 1900 includes an engagement surface 1916 and a plurality of recesses 1912. The head 1902 is configured to be disposed in the opening 1104 in one or more trajectories with respect to the seat 1216. More specifically, because of the matching configuration of the head 1902 to the opening 1104, the head 1902 can be pivoted and rotated in the opening 1104.

Accordingly, the geometry of the head 1902 is configured similarly to the geometry of the opening 1104, enabling the head 1902 of the screw 1900 to pivot and rotate in the opening 1104 and to be secured in the opening 1104 (as well as other openings) of the plate body 1102 in one or more trajectories.

The top surface 1914 is configured to be approximately planar or recessed with respect to a seat 1216 of the recess 1106 when the head 1902 is disposed in opening 1104. In various embodiments, the truncated sphere 1904 can be defined by the diameters 1906, 1908 such that the top surface 1914 of the head 1902 is approximately planar with or recessed below the seat 1216. Recessing the top surface 1914 of the head 1902 can provide a greater number of trajectories through the openings 1104 as well as keeping a low profile of the spinal plate 1100 and cap.

The engagement surface 1916 is arcuate and extends approximately centrally above the top surface 1914. The engagement surface 1916 is configured to approximate a center of the sphere 1904 that defines the head 1902. The engagement surface 1916 is further configured to engage a cap (e.g., crescent-shaped cap 1300, 2300), such that the screw head 1902 is pressed via approximately its center into at least a portion of the opening 1104 to secure the screw 1900 with respect to the spinal plate 1100 in a selected trajectory.

The engagement surface 1916 is defined by approximately hemisphere (or a different portion of a sphere) 1920 that extends approximately centrally above the top surface 1914. The engagement surface 1916 approximates the center of the sphere 1904. More specifically, the centers of the spheres 1904, 1920 are approximately concentric, e.g., the center of sphere 1920 approximates the center of the sphere 1904. Accordingly, the screw head 1902 (sphere 1904) can be pressed through approximately its center via the center of sphere 1920 into at least a portion of the opening 1104 to secure the screw 1900 with respect to the spinal plate 1100 in a selected trajectory. The sphere 1920 can be any dimension such that its center is approximately concentrically disposed in relation to the center of the sphere 1904.

The recesses 1912 are configured to engage reciprocal extensions of a driving tool (not shown) that can be used to drive (rotate) the screw 1900 into a vertebra of the spinal segment to be engaged. The recesses 1912 can be disposed at various locations about the periphery of the top surface 1914. In some embodiments as illustrated in FIG. 19, three recesses are equidistantly disposed about the engagement surface 1916. In other embodiments, more or less than three recesses—which are equidistantly or variously spaced about the periphery of the top surface 1914—can be provided.

The body 1924 of the screw 1900 includes a shaft 1926, thread 1928 and tip 1930. The thread 1928 is provided along a portion of the shaft 1926 below the head 1902, such that the screw 1900 can be disposed in the opening 1104 of the plate body 1102 in a plurality of trajectories and such that the screw 1900 can engage the vertebra. The thread 1928 is configured for self-cutting into the vertebra. The tip 1930 is self-cutting to facilitate the screw 1900 in penetrating the vertebra. The vertebra can also be pre-drilled to enable easier penetration into the vertebra. The body 1924 can also be similar to body 424 of screw 400 illustrated in FIG. 4.

Figure 20:
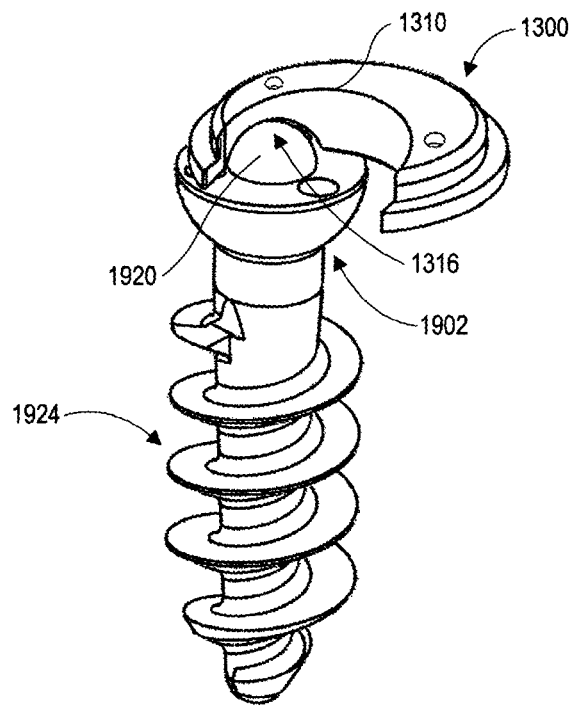
FIG. 20 illustrates a perspective view of the screw of FIG. 19 engaging a compression ramp of the crescent-shaped cap of FIG. 13.

FIG. 20 illustrates a perspective view of the screw 1900 engaging compression ramp 1316 of the crescent-shaped cap 1300.

The compression ramp 1316 approximates the engagement surface 1916 (e.g., sphere 1920) of the screw 1900. The compression ramp 1316 can be adjusted as required based on the dimensions of the engagement surface 1916.

It is assumed that the screw 1900—in the screw-loading alignment—has been received through the aligned opening 1310 of the crescent-shaped cap 1300 and opening 1104 in the plate body 1102, has further been pivoted into a selected trajectory through the plate body 1102, and then rotated (threaded) via body 1924 into the vertebra in the selected trajectory.

Once the body 1924 of the screw 1900 has engaged the vertebra securely through the opening 1104 in the selected trajectory, the head 1902 of the screw 1900 engages at least a portion of the opening 1104 in the plate body 1102 of the spinal plate 1100. The crescent-shaped cap 1300 is thereafter rotated in the recess 1106 of the plate body 1102 from the screw-loading alignment into the screw-compression alignment.

The compression ramp 1316 is configured to engage the engagement surface 1916 of the screw 1900 and to progressively compress the engagement surface 1916 of the screw 400 as the crescent-shaped cap 1300 rotates between the screw-loading alignment and the screw-compression alignment.

Figure 21:
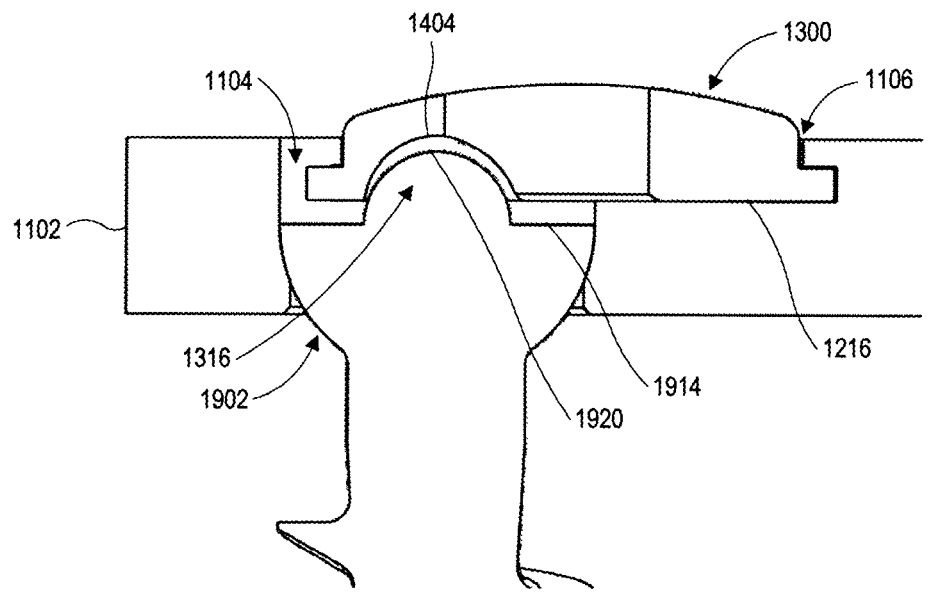
FIG. 21 illustrates a cross-sectional view of the example crescent-shaped cap of FIG. 13 between the screw-loading alignment and the screw-compression alignment with respect to the opening of FIG. 12 and the screw of FIG. 19.

FIG. 21 illustrates a cross-sectional view of the example crescent-shaped cap 1300 between the screw-loading alignment and the screw-compression alignment with respect to the opening 1104 in the plate body 1102 and screw 1900.

The compression ramp 1316 of the crescent-shaped cap 1300 rides over the engagement surface 1916 as the crescent-shaped cap 1300 is rotated in the recess 1106, with the ramped surface 1404 progressively increasing compression along its path and the ridge 1406 (shown in FIG. 22) providing the most compression on the engagement surface 1916 of the screw 1900, until the locking recess 1408 (shown in FIG. 22) engages the engagement surface 1916 (or a portion thereof) past the ridge 1406.

Figure 22:
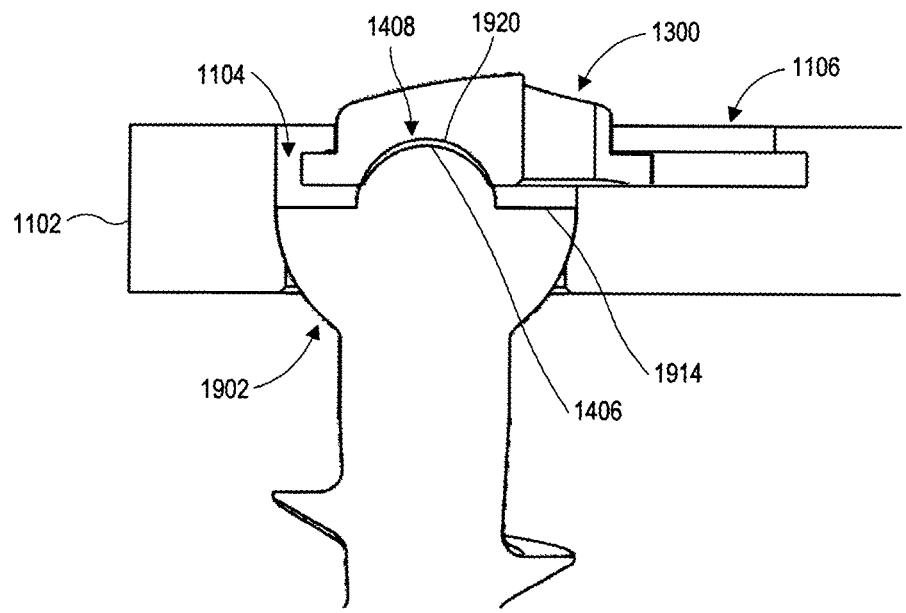
FIG. 22 illustrates a cross-sectional view of the example crescent-shaped cap of FIG. 13 in the screw-compression alignment with respect to the screw of FIG. 19 in the opening of FIG. 12.

FIG. 22 illustrates a cross-sectional view of the example crescent-shaped cap 1300 in the screw-compression alignment with respect to the screw 1900 in the opening 1104 of the plate body 1102.

The compression ramp 1316 rides over the engagement surface 1916 (e.g., sphere 1920) as the crescent-shaped cap 1300 is rotated in the recess 1106 between the screw-loading alignment and the screw-compression alignment with respect to the opening 1104. The ramped surface 1404 of the compression ramp 1316 progressively increases compression along its path until ridge 1406. Thereafter, the engagement surface 1916 (or a portion thereof) engages the locking recess 1408.

The locking recess 1408 compresses the engagement surface 1916 of the screw 1900—in which compression of sphere 1920 compresses the head 1902 (sphere 1904) of the screw 1900 because as the centers of spheres 1904, 1920 are approximately concentric—into the engaged portion of the opening 1104 in the selected trajectory.

Figure 23:
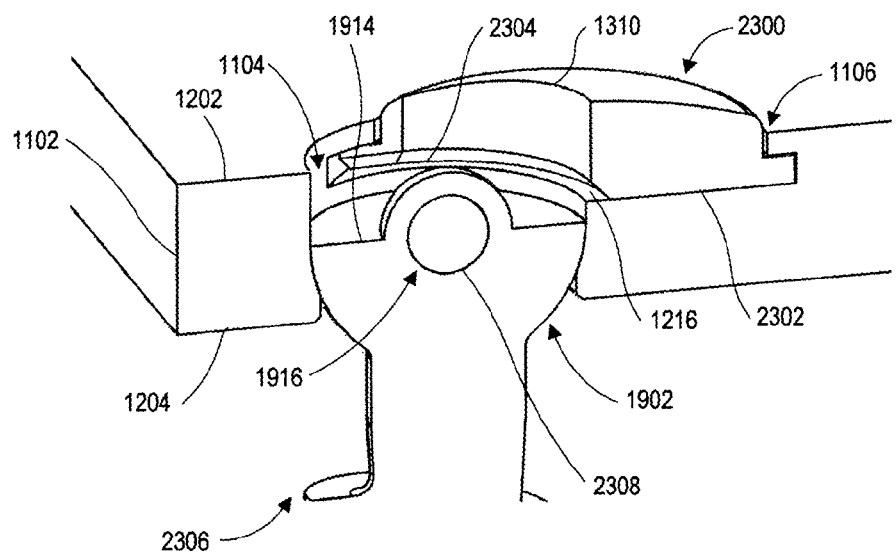
FIG. 23 illustrates perspective view of an example crescent-shaped cap engaging the recess of FIG. 12 in the screw-loading alignment with respect to an example screw having a deformable portion.

FIG. 23 illustrates perspective view of an example a crescent-shaped cap 2300 engaging the recess 1106 of the spinal plate 1100 in the screw-loading alignment with respect to an example screw 2306.

The configuration of the crescent-shaped cap 2300 is similar to crescent-shaped cap 1300, except as follows. The crescent-shaped cap 2300 omits the compression ramp 1316. Instead, the crescent-shaped cap 2300 includes bottom surface 2302 and chamfer 2304. The bottom surface 2302 is configured to mate in a planar configuration with seat 1216 of the recess 1106. The chamfer 2304 is configured to facilitate engagement of the crescent-shaped cap 2300 with the engagement surface 1916 of the screw 2306. Further the crescent-shaped cap 2300 is approximately planar with the top surface 1202 of the plate 1102, providing a lower profile configuration.

The configuration of the screw 2306 is similar to screw 1900, except as follows. The engagement surface 1916 of the screw 2306 can deform to accommodate dimensional differences between the screw 2306, opening 1104 and crescent-shaped cap 2300. The screw 2306 can be made of similar materials described herein with reference to screws 400, 1900 of FIGS. 4 and 19, respectively.

More specifically, the sphere 1920 can include a deformable portion 2308 that can be deformed by engagement with the crescent-shaped cap 2300. The compressible portion 2308 can be a hollow space or can be a material that is resilient yet compressible (e.g., PEEK).

In the screw-loading alignment, the opening 1310 of the crescent-shaped cap 2300 approximates the opening 1104 in the plate body 1102 of the spinal plate 1100. The screw 2306 has been inserted through the opening 1310 into the opening 1104. Furthermore, the screw 2306 has been threaded via recesses 1912 (shown in FIG. 24) into the vertebra of the spinal segment in the selected trajectory. The head 1902 of the screw 2306 engages at least a portion of the opening 1104 of the plate body 1102.

The engagement surface 1916 of the screw 2306 extends at least partially into the recess 1106. The chamfer 2304 at the opening 1310 generally approximates the extension of the engagement surface 1916 into the recess 1106, such that the bottom 2302 of the crescent-shaped cap 2300 can engage and deform the engagement surface 1916 as the crescent-shaped cap 2300 is rotated from the screw-loading alignment into screw-compression alignment.

Figure 24:
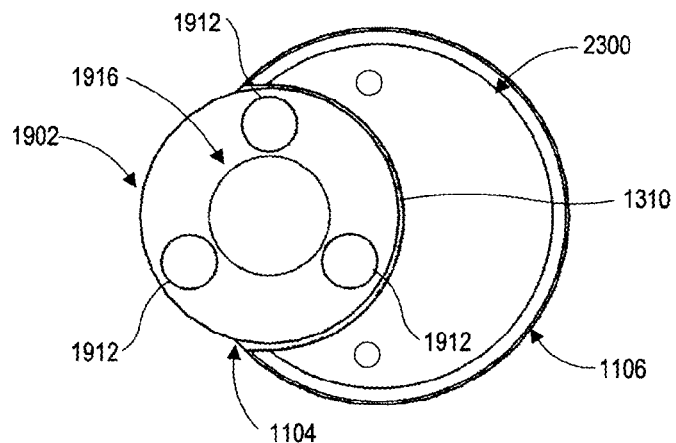
FIG. 24 illustrates a top view of the crescent-shaped cap of FIG. 23 engaging the recess of FIG. 12 in a screw-loading alignment with respect to the screw of FIG. 23.

FIG. 24 illustrates a top view of the crescent-shaped cap 2300 engaging the recess 1106 in a screw-loading alignment.

In the screw-loading alignment, the alignment opening 1310 in the crescent-shaped cap 2300 approximates the opening 1104 in the plate body 1102, allowing receipt of the screw 2306 into the opening 1104, pivoting of the head 1902 of the screw 2306 in the opening 1104 into a selected trajectory, and rotation of the body 424 of the screw 2306 into the vertebra in the selected trajectory through the crescent-shaped cap 2300.

As illustrated in FIG. 24, the screw 2306 has been inserted through the cap 2300 into the opening 1104 and threaded into the vertebra of the spinal segment in the selected trajectory with respect to the plate body 1102.

Because of the matching configuration of the screw head 1902 and the opening 1104, the screw 2306 can be received in the opening 1104 in one of many trajectories so that the vertebra can be engaged (threaded) in the trajectory that is advantageous for better engagement. Recesses 1912 in the head 402 are used to thread the screw 2306 into the vertebra in the selected trajectory.

The engagement surface 1916 of the screw 2306 extends at least partially into the recess 1106. The chamfer 2304 at the alignment opening 1310 generally approximates the extension of the engagement surface 1916 in the recess 1106, such that crescent-shaped cap 2300 can slide over and engage the engagement surface 1916.

Figure 25:
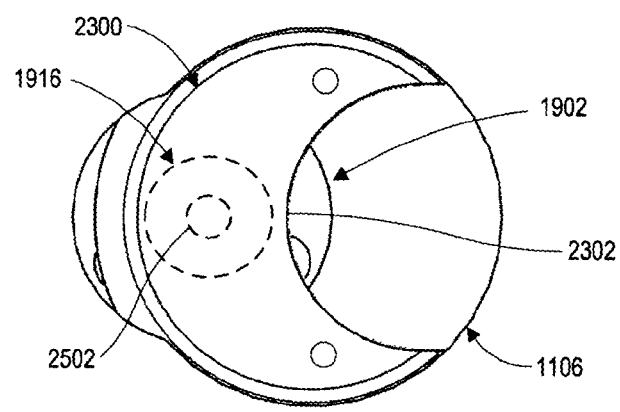
FIG. 25 illustrates a perspective view of the crescent-shaped cap of FIG. 23 engaging the recess of FIG. 12 in a screw-compression alignment with respect to the screw of FIG. 23.

FIG. 25 illustrates a perspective view of the crescent-shaped cap 2300 engaging the recess 1106 of the spinal plate 1100 in a screw-compression alignment.

Once the body 1924 of the screw 2306 has engaged the vertebra securely through opening 1104 in the selected trajectory, the head 1902 of the screw 2306 engages at least a portion of the opening 1104 in the plate body 1102 of the spinal plate 1100. The crescent-shaped cap 2300 is thereafter rotated in the recess 1106 from the screw-loading alignment into the screw-compression alignment.

The rotation of the crescent-shaped cap 2300 in the recess 1106 from the screw-loading alignment into the screw-compression alignment deforms engagement surface 1916, compressing the head 1902 of the screw 2306 via engagement surface 1916 into the engaged portion of the opening 1104 of the plate body 102 in the selected trajectory.

Generally, the screw-compression alignment can be at any location along the bottom 2302 of the crescent-shaped cap 2300. However, in order to cover a substantial portion of screw head 1902 in the screw-compression alignment, the crescent-shaped cap 2300 is rotated up to approximately 180 degrees with respect to the screw-loading alignment. In various embodiments, these alignments can be different.

In the screw-compression alignment, the engagement surface 1916 is deformed to form engagement surface 2502. The engagement surface 2502 not only compresses the head 1902 into the opening 1104 but also engages bottom surface 2302 of the crescent-shaped cap 2300 across a larger contact area in the selected trajectory. This mitigates the wobbling of polyaxial screws in the openings of prior art spinal plates. The screw 2306 does not wobble in the opening 1104 if and when the body 1924 of the screw 2306 loosens with respect to the vertebra. Similarly, the body 1924 is also less likely to loosen with respect to the vertebrae.

Figure 26:
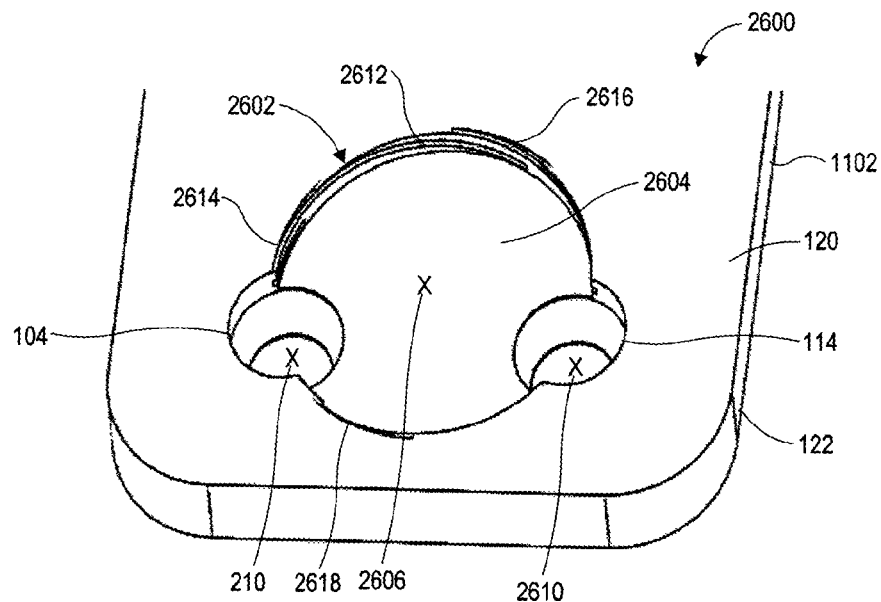
FIG. 26 illustrates perspective view of an example recess in the plate body of FIG. 1 that is eccentric (off-center) with reference to multiple openings of FIG. 1.

FIG. 26 illustrates perspective view of an example recess 2602 in the plate body 102 that is eccentric (off-center) with reference to the openings 104, 114. The recess 2602 has a center 2606, and seat 2604 and threading 2612.

Whereas openings 104, 114 extend though the plate body 102, the recess 2602 extends partially into the plate body 102. The center 2606 of the recess 2602 is off-center (eccentric) with reference to the centers 2608, 2610 of the opening 104, 114, respectively. The openings 104, 114 are configured to receive screws 400 and can also be configured similarly to the opening 1104 described in detained hereinabove with reference to FIG. 12.

The recess 2602 intersects the openings 104, 114, such that only a portion of the openings 104, 114 is encompassed inside the recess 2602, including at least the centers 210, 2610 of the respective openings 104, 114.

In some embodiments, openings 104, 114 are encompassed in the recess 2602, where no point in the circumferences of the openings 104, 114 touches any other point in the circumference of the recess 2602. In other embodiments, at least one point in the circumferences of the openings 104, 114 touches at least another point in the circumference of the recess 2602. One or more other recesses—similar to recess 2602—can be provided in the plate body 102 with reference pairs of openings 106-112 in FIG. 1.

The seat 2604 is generally a planar surface below the top surface 120 and above the bottom surface 122 of the plate body 102. The seat 2604 can be, but does not have to be, parallel to the surfaces 120, 122 of the plate body 102 depending on the configuration of the plate body 102. The seat 2604 is configured to provide a final stop to threaded cap 2700 described in greater detail below with reference to FIGS. 27-29.

Figure 27:
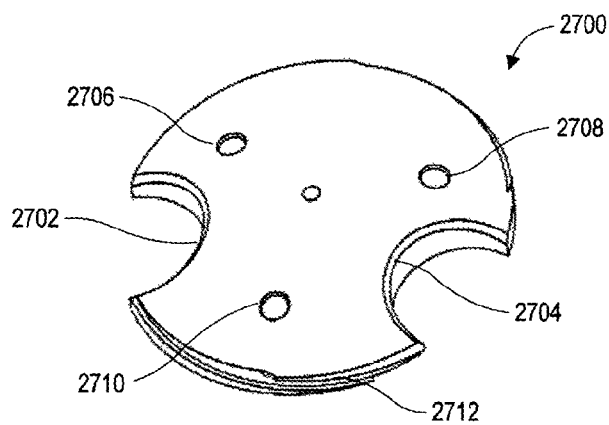
FIG. 27 illustrates a perspective top view of a threaded cap configured to be disposed in one or more alignment positions with respect to the recess illustrated in FIG. 26.

The threading 2612 is formed along the circumference of the recess 2602 and is configured to threadably engage the threaded cap 2700 of FIG. 27, such that the threaded cap 2700 can be inserted (screwed) into and removed (unscrewed) from the recess 2602. The seat 2604 provides the inner-most extent to which the threaded cap 2700 can be inserted in the recess 2602. In some embodiments, the threaded cap s700 can also rotate in-plane with respect to the recess 2602, as described with reference to FIG. 2.

The threading 2612 (lead, form and other factors) is configured such that any possible motion (wobble) of the screws 400 in the openings 104, 114 is less likely to be converted to rotary motion, further mitigating the possibility of the threaded cap 2700 from being unscrewed from the threading 2612 of the recess 2602.

The threading 2612 includes thread alignment (engagement) slots 2614-2618, which are configured to receive reciprocal thread extensions 2802-2806 of the threaded cap 2700 (shown in FIG. 28), such that the threaded cap 2700 can be received in alignment with respect to the threading 2612. The alignment slots 2614-2618 represent respective starts to the threading 2612 of the recess 2602. The number and configuration of the alignment slots 2614-2618 can be adjusted based on the respective number and configuration of the 2802-2806. The foregoing alignment enables precise alignment of the threaded cap 2700 and the recess 2602 into a screw-loading alignment and screw-compression alignment with rotation of the threaded cap 2700 in the recess 2602.

FIG. 27 illustrates a perspective top view of a threaded cap 2700 that is configured to be disposed in one or more alignment positions with respect to the recess 2602 in the plate body 102 illustrated in FIG. 26.

The threaded cap 2700 can be made a metal (e.g., titanium, stainless steel, or other metal), polyethylethylketone (PEEK), ceramic material, bio-absorbable material, other medically-surgically acceptable material, and combinations of these and/or conventional or later-developed suitable materials that are resilient yet durable to withstand movement of the vertebrae. The threaded cap 2700 includes alignment openings 2702, 2704, openings 2706-2710, and threading 2712.

The openings 2706-2710 are configured to engage respective extensions of a tool (e.g., prong screw driver) to threadably engage the threading 2712 of the threaded cap 2700 with the threading 2612 of the recess 2602, and further to rotate the threaded cap 2700 in the recess 2602 between a screw-loading alignment and a screw-compression alignment. Instead of the openings 2706-2710, a different engagement mechanism can be used to engage threading 2712 of threaded cap 2700 with threading 2612 of the opening 2602.

In the screw-loading alignment, the alignment openings 2702, 2704 approximate the respective openings 104, 114, enabling the receipt of the screws 400 (or other screws, such as screws 1900 or 2306) through the threaded cap 2700 into the openings 104, 114, pivoting of the head 402 of the screws 400 in the openings 104, 114 into selected trajectories, and rotation (threading) of the screws 400 into a vertebra or vertebrae through the threaded cap 2700 in the selected trajectories.

It is noted that, that because of the matching configuration of the head 402 of the screws and the openings 104, 114 and the alignment of the openings 104, 114 and the openings 2702, 2704, the screws 400 can be threaded into the vertebra through the plate body 102 of the spinal plate 100 in one of many trajectories, as may be advantageous in order to achieve better engagement with the vertebra or vertebrae.

Figure 28:
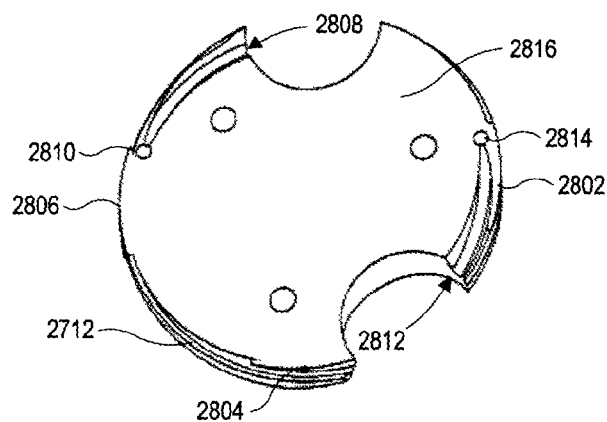
FIG. 28 illustrates a perspective bottom view of the threaded cap illustrated in FIG. 27.

FIG. 28 illustrates a perspective bottom view of the threaded cap 2700 illustrated in FIG. 27.

The threaded cap 2700 further includes thread extensions (starts) 2802-2806, planar bottom surface 2816, compression ramps 2808, 2812, and recesses (detents) 2810, 2814.

The thread extensions 2802-2806 are a part (starts) of the threading 2712 and are disposed about the circumference of the threaded cap 2700. The thread extensions 2802-2806 are sized and dimensioned to be received in respective alignment slots 2614-2618. Further, the extensions 2802-2806 are configured to enable engagement of threading 2712 of threaded cap 2700 with threading 2612 of the recess 2602, such that the threaded cap 2700 can screw into the recess 2602 via the threading 2612. In some embodiments, more or fewer extensions (starts) in the threaded cap 2700 and respective alignment slots in the recess 2602 can be provided. For example, two or four extensions and respective alignment slots can be provided.

In some embodiments, the bottom surface 2816 can mate in a planar configuration with the seat 2604 of the recess 2602.

The compression ramps 2808, 2812 are configured to approximate and progressively compresses or engage the engagement surfaces 416 of the screws 400, such that the heads 402 of the screws 400 can be compressed into engaged portions of the openings 104, 114, as the threaded cap 2700 rotates between the screw-loading alignment and the screw-compression alignment in the recess 2602.

The recesses (detents) 2810, 2814 of respective compression ramps 2802, 2812 approximate the engagement surfaces 416 of the screws 400 and are configured to receive at least portions of the engagement surfaces 416 in a compression engagement with respect to the openings 104, 114. In some embodiments, the recesses 2810, 2814 are configured to accommodate at least a portion of the spheres 420 of the engagement surfaces 416. The recesses 2810, 2814 can provide a clicking that indicates successful compression engagement.

Furthermore, recesses 2810, 2814 mitigate any possible motion (wobble) of the heads 402 of screws 400 in the respective openings 104, 114 and about the engagement surface 2816, such that it is less likely that such motion is converted to rotary motion that can unscrew the threaded cap 2700 from the recess 2602.

Figure 29:
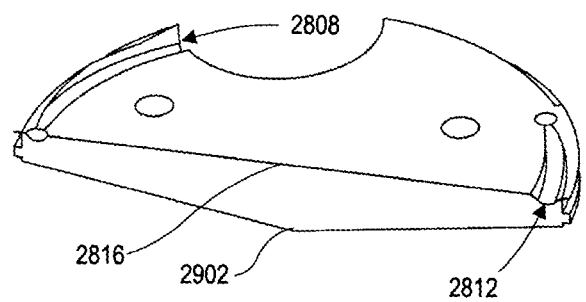
FIG. 29 illustrates a cross-sectional view of the threaded cap illustrated in FIG. 27.

FIG. 29 illustrates a cross-sectional view of the threaded cap 2700 illustrated in FIG. 27. As illustrated, the bottom surface 2816 is planar, while the top 2902 is developed or sloped (cone-shaped) around a center 2902.

The compression ramps 2808, 2812 are disposed along the engagement path that the engagement surfaces 416 of the screws 400 follow as the threaded cap 2700 is rotated in the recess 2602. As the threaded cap 2700 is rotated into the screw-compression alignment, the compression ramps 2808, 2812 engage at least portions of engagement surfaces 416 of the screws 400, engaging the screw heads 402 into at least portions of the openings 104, 114. In some embodiments, the compression ramps 2808, 2812 compressively engage at least portions of the spheres 420 and the recesses 2810, 2814 engage at least portions of the spheres 420.

Figure 30:
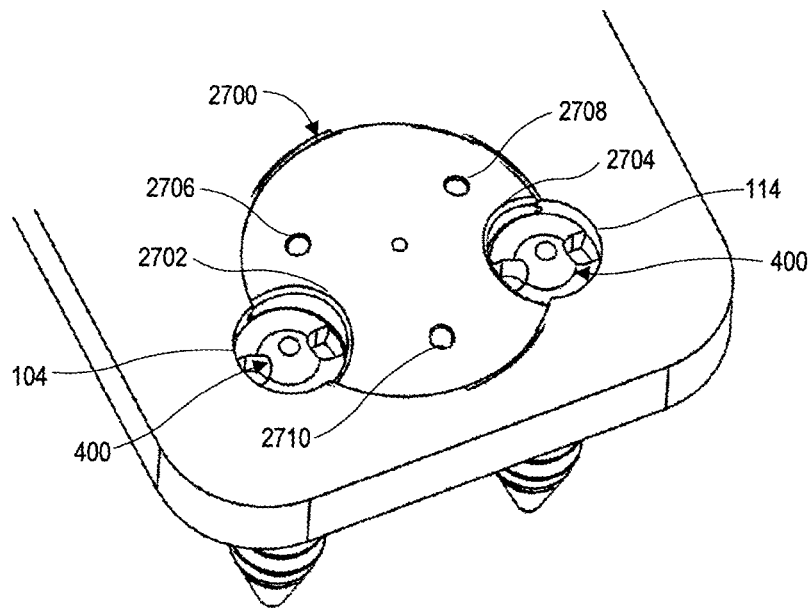
FIG. 30 illustrates a perspective view of the threaded cap of FIG. 27 engaging threading of the recess of FIG. 26 in a screw-loading alignment.

FIG. 30 illustrates a perspective view of a threaded cap 2700 engaging threading 2612 of the recess 2602 in a screw-loading alignment.

The extensions 2802-2806 of the threaded cap 2700 have been received via respective alignment slots 2614-2618 into the recess 2602. Furthermore, the threaded cap 2700 has been rotated (threaded) at least partially via the openings 2706-2710 to engage the threading 2712 with the threading 2612 and to align the alignment openings 2702, 2704 of the threaded cap 2700 with the respective openings 104, 114 of the plate body 102 in the screw-loading alignment.

It is to be noted that the spinal plate 100 with the threaded cap 2700 engaging the recess 2602 in the screw-loading alignment is inserted into position with respect to the vertebrae of spinal segment to be fixated via the spinal plate 100. Additional caps 2700 in relation to one or more of the other pairs of openings 106-112 are also engaged in screw-loading alignment before insertion of the plate 100 into position with respect to the spinal segment to be fixated. In alternate embodiments, the spinal plate 100 and the treaded cap 2700 can be inserted separately.

In the screw-loading alignment, the alignment openings 2702, 2704 of the threaded cap 2700 allow receipt of the screws 400 through the threaded cap 2700 into the openings 104, 114, pivoting of the heads 402 of the screws 400 in the openings 104, 114 into selected trajectories, and rotation (threading) of the bodies 424 of the screws 400 into the vertebra or vertebrae in the selected trajectories through the threaded cap 2700 via recesses 412 of the screws 400. Because of the matching configuration of the screw heads 402 and the openings 104, 114, the screws 400 can be threaded into the vertebra or vertebrae of the spinal segment through the plate body 102 in various trajectories, as may be advantageous in order to achieve better engagement with the vertebra or vertebrae.

Figure 31:
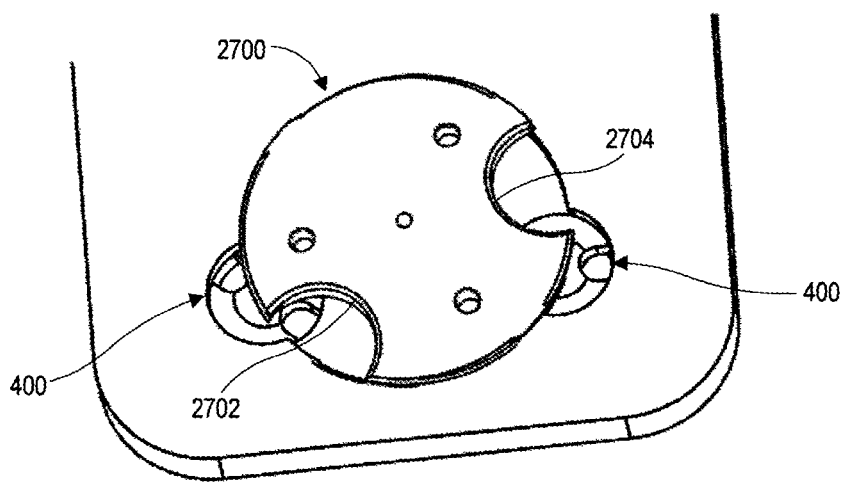
FIG. 31 illustrates a perspective view of a threaded cap of FIG. 27 engaging threading of the recess of FIG. 26 in a screw-compression alignment.

FIG. 31 illustrates a perspective view of a threaded cap 2700 engaging threading 2612 of the recess 2602 in a screw-compression alignment.

Once the screws 400 have engaged the vertebra or vertebrae securely through openings 104, 114, the heads 402 of the screws 400 engage at least portions of the openings 104, 114 of the plate body 102. Thereafter, the threaded cap 2700 is rotated (e.g., threaded) in the recess 2602 from the screw-loading alignment into a screw-compression alignment. The rotation of the threaded cap 2700 progressively compresses the heads 402 of the screws 400 via engagement surfaces 416 into the engage portions of the openings 104, 114 of the plate body 102 in the selected trajectories as described below.

More specifically, the compression ramps 2808, 2812 progressively compress the heads 402 of the screws into the openings 104, 114 until the recesses (detents) 2810, 2814 engage the engagement surfaces 416 of the screw heads 402 in the screw-compression alignment. The recesses (detents) 2810, 2814 also compress the engagement surfaces 416 of the screw heads 402 in the screw-compression alignment. Generally, the screw-compression alignment can be approximately up to 180 degrees or less with respect to the screw-loading alignment. In various embodiments, these alignments can be different.

In the screw-compression alignment, the threaded cap 2700 engages the engagement surfaces 416 of the heads 402 of the screws 400 via recesses 2810, 2814, compressing the screw heads 402 (spheres 404) of the screws 400 into the engaged portions of the openings 104, 114 in the selected trajectories via the spheres 420 of the engagement surfaces 416. This mitigates the wobbling of poly-axial screws in the openings of prior art spinal plates. The screws 400 do not wobble in the openings 104, 114 if and when the bodies 424 of the screws 400 loosen with respect to the vertebra or vertebrae. Similarly, the bodies 424 are less likely to loosen with respect to the vertebrae.

Figure 32:
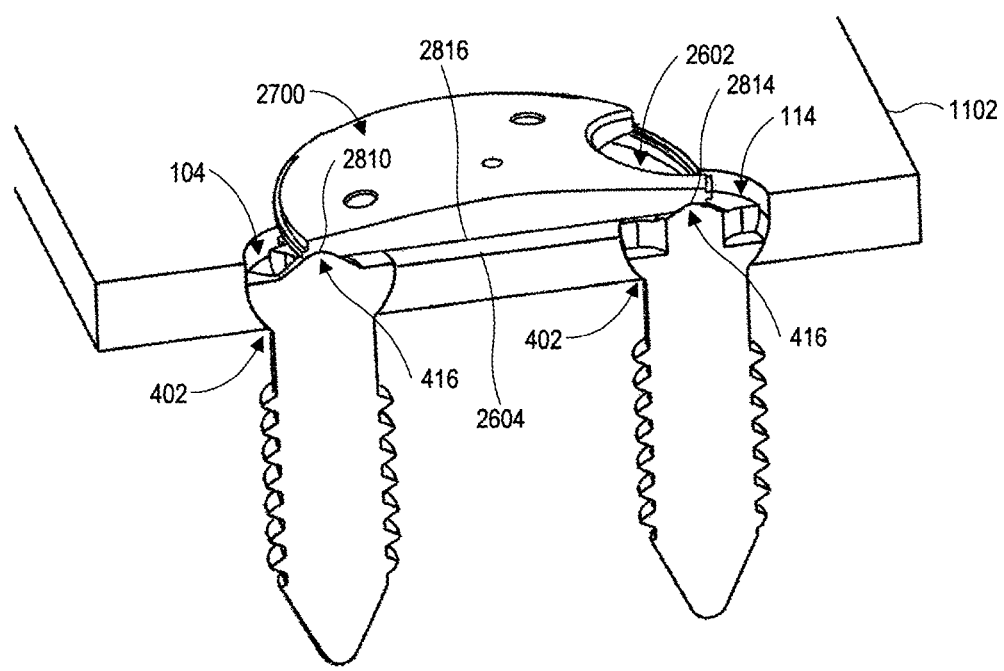
FIG. 32 illustrates a cross-sectional view of a threaded cap of FIG. 27 engaging threading of recess of FIG. 26 in the screw-compression alignment.

FIG. 32 illustrates a cross-sectional view of a threaded cap 2700 engaging threading 2612 of recess 2602 in the screw-compression alignment.

It is noted that the screws 400 have been received through the aligned threaded cap 2700 and the openings 104, 114. Trajectories for the screws 400 in relation to the vertebra(e) have been selected and the screws 400 threaded into the vertebra or vertebrae to secure the plate 100 to the vertebra(e) via the openings 104, 114. The screw heads 402 of the screws 400 engage at least portion of the openings 104, 114 in the selected trajectories.

Thereafter, the threaded cap 2700 is advanced further in the recess 2602 into the screw-compression alignment in which the threaded cap 2700 engages the engagement surfaces 416 (spheres 420) of the heads 402 via recesses 2810, 2814, compressing the screw heads 402 (spheres 404) of the screws 400 into the engaged portion of the openings 104, 114 in the selected trajectories via spheres 420 of the engagement surfaces 416. This compression reduces or eliminates the wobbling of the screws 400 in the openings 104, 114 if and when the screws 400 loosen with respect to the vertebra(e).

In the screw-compression alignment, the bottom surface 2816 of the threaded cap 2700 can be at distance to the seat 2604 or can engage the seat 2604 in order to provide friction, counteracting any unscrewing forces that can compel the threaded cap 2700 from the recess 2602.

Thus, a spinal plate with compression locking and a method of fixating vertebrae using the spinal plate with compression locking have been described. Although specific example embodiments have been described, it will be evident that various modifications and changes can be made to these embodiments without departing from the broader scope of this application. Accordingly, the specification and drawings are to be regarded in an illustrative rather than a restrictive sense. The accompanying drawings that form a part hereof, show by way of illustration, and not of limitation, specific embodiments in which the subject matter can be practiced. The embodiments illustrated are described in sufficient detail to enable those skilled in the art to practice the teachings disclosed herein. Other embodiments can be utilized and derived therefrom, such that structural substitutions and changes can be made without departing from the scope of this application. This Detailed Description, therefore, is not to be taken in a limiting sense, and the scope of various embodiments is defined only by the appended claims, along with the full range of equivalents to which such claims are entitled.

Such embodiments of the inventive subject matter can be referred to herein, individually and/or collectively, by the term "invention" merely for convenience and without intending to voluntarily limit the scope of this application to any single invention, inventive concept or embodiment. Thus, although specific embodiments have been illustrated and described herein, it should be appreciated that any arrangement calculated to achieve the same purpose can be substituted for the specific embodiments shown. This application is intended to cover any and all adaptations or variations of various embodiments. Combinations of the above embodiments and other embodiments not specifically described herein, will be apparent to those of skill in the art upon reviewing the above description.

The Abstract is provided to comply with 37 C.F.R. §1.72(b) and will allow the reader to quickly ascertain the nature of the technical disclosure of this application. It is submitted with the understanding that it will not be used to interpret or limit the scope or meaning of the claims.

In the foregoing description of the embodiments, various features can be grouped together in a single embodiment for the purpose of streamlining the disclosure of this application. This method of disclosure is not to be interpreted as reflecting that the claimed embodiments have more features than are expressly recited in each claim. Rather, as the following claims reflect, inventive subject matter lies in less than all features of a single disclosed embodiment.

What is claimed is:

1. A spinal plate system, the system comprising:
   a screw including a head and a threaded body, the head including a portion of a first sphere that has a first center and a portion of a second sphere that has a second center approximately concentric with the first center, the body extending from the portion of the first sphere;
   a spinal plate including an opening through the spinal plate and an associated recess in the spinal plate that is eccentric with the opening; and
   a cap including an alignment opening, the cap configured to be rotationally engaged in the recess between a first rotational configuration and a second rotational configuration, the first rotational configuration enabling the threaded body to be threaded into a vertebra in a selected trajectory through the alignment opening and the opening in the spinal plate and the head to engage at least a portion of the opening in the selected trajectory, the second rotational configuration enabling the cap to compress the portion of the second sphere into the portion of the first sphere approximately through its center such that the head is compressed into the engaged portion of the opening.

2. The spinal plate system of claim 1, wherein the head further includes a cylinder disposed atop the portion of the first sphere, the cylinder being within or circumscribed by the first sphere and including a top surface.

3. The spinal plate system of claim 2, wherein the head further includes a truncated cone disposed approximately centrally with respect to the portion of the first sphere between the top surface of the cylinder and the portion of the second sphere.

4. The spinal plate system of claim 2, wherein the head further includes a plurality of recesses about and through the periphery of the top surface and extending into the portion of the first sphere, the recesses being configured to rotate the screw.

5. The spinal plate system of claim 2, wherein the portion of the second sphere includes a deformable portion configured to be deformed when the cap is rotated between the first rotational configuration and the second rotational configuration.

6. The spinal plate system of claim 1, wherein the opening through the spinal plate is within the associated recess in the spinal plate.

7. The spinal plate system of claim 1, wherein the opening through the spinal plate intersects the associated recess in the spinal plate.

8. The spinal plate system of claim 1, wherein the opening through the spinal plate approximates the configuration of the portion of the first sphere.

9. The spinal plate system of claim 1, wherein at least a portion of the opening through the spinal plate approximates the configuration of the portion of the first sphere.

10. The spinal plate system of claim 9, wherein the opening includes a first cylindrical opening extending through a bottom surface of the spinal plate partially into the spinal plate, a second cylindrical opening extending through the recess partially into the spinal plate, and a spherically-shaped opening between the first cylindrical opening and the second cylindrical opening, the spherically-shaped opening approximating the configuration of the portion of the first sphere of the head.

11. The spinal plate system of claim 1,
    wherein the recess includes first threading and a plurality of thread alignment slots; and
    wherein the cap includes a second threading and a plurality of thread extensions, such that the thread extensions are receivable into the respective thread alignment slots to enable engagement of the second threading with the first threading.

12. The spinal plate system of claim 1,
    wherein the recess includes an extension about a portion of a periphery of the recess that forms a channel about the portion of the periphery; and
    wherein the cap includes a lip about a portion of its circumference such that the cap is rotationally disposed in the channel.

13. The spinal plate system of claim 1, wherein the cap includes a plurality of openings configured to engage and to rotate the threaded cap in the recess between the first rotational configuration and the second rotational configuration.

14. The spinal plate system of claim 1, wherein the alignment opening is within a circumference of the cap.

15. The spinal plate system of claim 1, wherein the alignment opening intersects a circumference of the cap.

16. The spinal plate system of claim 1, wherein the cap includes a compression ramp that is configured to progressively compress the head into the engaged portion of the opening as the cap is rotated in the recess between the first rotational configuration and the second rotational configuration.

17. The spinal plate system of claim 16, wherein compression ramp includes a recess configured to receive in a compression engagement at least the portion of the second sphere.

* * * * *